(12) United States Patent
Pathak et al.

(10) Patent No.: US 7,597,882 B2
(45) Date of Patent: Oct. 6, 2009

(54) PROTEIN CROSSLINKERS, CROSSLINKING METHODS AND APPLICATIONS THEREOF

(75) Inventors: Chandrashekhar P. Pathak, Phoenix, AZ (US); Amarpreet S. Sawhney, Lexington, MA (US); James H. Dreher, Santa Monica, CA (US)

(73) Assignee: Incept LLC, Lexington, MA (US)

( * ) Notice: Subject to any disclaimer, the term of this patent is extended or adjusted under 35 U.S.C. 154(b) by 0 days.

(21) Appl. No.: 11/789,459

(22) Filed: Apr. 24, 2007

(65) Prior Publication Data

US 2007/0248567 A1  Oct. 25, 2007

Related U.S. Application Data

(60) Provisional application No. 60/794,384, filed on Apr. 24, 2006.

(51) Int. Cl.
*A61K 31/74* (2006.01)
*C08F 283/00* (2006.01)
*C07K 14/00* (2006.01)

(52) U.S. Cl. .................. 424/78.27; 525/54.1; 530/350; 530/380; 530/402

(58) Field of Classification Search .............. 424/78.27; 525/54.1; 530/350, 380, 402
See application file for complete search history.

(56) References Cited

U.S. PATENT DOCUMENTS

| | | | |
|---|---|---|---|
| 4,359,049 A | 11/1982 | Redl et al. | |
| 4,631,055 A | 12/1986 | Redl et al. | |
| 4,735,616 A | 4/1988 | Eibl et al. | |
| 4,874,368 A | 10/1989 | Miller et al. | |
| 4,902,281 A | 2/1990 | Avoy | |
| 4,932,942 A | 6/1990 | Maslanka | |
| 4,978,336 A | 12/1990 | Capozzi et al. | |
| 5,116,315 A | 5/1992 | Capozzi et al. | |
| 5,122,614 A | 6/1992 | Zalpisky | |
| 5,162,430 A | 11/1992 | Rhee et al. | |
| 5,213,808 A | 5/1993 | Bar-Shalom et al. | |
| 5,219,564 A | 6/1993 | Zalpisky et al. | |
| 5,304,595 A | 4/1994 | Rhee et al. | |
| 5,324,775 A | 6/1994 | Rhee et al. | |
| 5,328,955 A | 7/1994 | Rhee et al. | |
| 5,410,016 A | 4/1995 | Hubbell et al. | |
| 5,413,791 A | 5/1995 | Rhee et al. | |
| 5,446,091 A | 8/1995 | Rhee et al. | |
| 5,455,027 A | 10/1995 | Zalpisky et al. | |
| 5,470,911 A | 11/1995 | Rhee et al. | |
| 5,475,052 A | 12/1995 | Rhee et al. | |
| 5,527,856 A | 6/1996 | Rhee et al. | |
| 5,529,914 A | 6/1996 | Hubbell et al. | |
| 5,540,707 A | 7/1996 | Ressemann et al. | |
| 5,550,187 A | 8/1996 | Rhee et al. | |
| 5,550,188 A | 8/1996 | Rhee et al. | |
| 5,565,519 A | 10/1996 | Rhee et al. | |
| 5,567,435 A | 10/1996 | Hubbell et al. | |
| 5,573,934 A | 11/1996 | Hubbell et al. | |
| 5,583,114 A | 12/1996 | Barrows et al. | |
| 5,614,587 A | 3/1997 | Rhee et al. | |
| 5,626,863 A | 5/1997 | Hubbell et al. | |
| 5,643,464 A | 7/1997 | Rhee et al. | |
| 5,744,545 A | 4/1998 | Rhee et al. | |
| 5,752,974 A | 5/1998 | Rhee et al. | |
| 5,786,421 A | 7/1998 | Rhee et al. | |
| 5,800,541 A | 9/1998 | Rhee et al. | |
| 5,801,033 A | 9/1998 | Hubbell et al. | |
| 5,844,016 A | 12/1998 | Sawhney et al. | |
| 5,858,746 A | 1/1999 | Hubbell et al. | |
| 5,874,500 A | 2/1999 | Rhee et al. | |
| 5,935,139 A | 8/1999 | Bates | |
| 5,986,043 A | 11/1999 | Hubbell et al. | |
| 6,050,972 A | 4/2000 | Zadno-Azizi et al. | |
| 6,051,248 A | 4/2000 | Sawhney et al. | |
| 6,051,648 A | 4/2000 | Rhee et al. | |
| 6,063,061 A | 5/2000 | Wallace et al. | |
| 6,065,645 A | 5/2000 | Sawhney et al. | |
| 6,132,986 A | 10/2000 | Pathak et al. | |
| 6,152,943 A | 11/2000 | Sawhney | |
| 6,153,211 A | 11/2000 | Hubbell et al. | |
| 6,156,531 A | 12/2000 | Pathak et al. | |
| 6,162,241 A | 12/2000 | Coury et al. | |
| 6,165,201 A | 12/2000 | Sawhney et al. | |
| 6,166,130 A | 12/2000 | Rhee et al. | |
| 6,176,871 B1 | 1/2001 | Pathak et al. | |
| 6,177,514 B1 | 1/2001 | Pathak et al. | |
| 6,179,862 B1 | 1/2001 | Sawhney | |
| 6,201,065 B1 | 3/2001 | Pathak et al. | |
| 6,306,922 B1 | 10/2001 | Hubbell et al. | |
| 6,312,725 B1 | 11/2001 | Wallace et al. | |
| 6,323,278 B2 | 11/2001 | Rhee et al. | |
| 6,326,419 B1 | 12/2001 | Smith | |
| 6,371,970 B1 | 4/2002 | Khosravi et al. | |

(Continued)

FOREIGN PATENT DOCUMENTS

EP  0732109 A1  9/1996

(Continued)

OTHER PUBLICATIONS

Hill-West et al., "Prevention of Postoperative Adhesions in the Rat by In Situ Photopolymerization of Bioresorbably Hydrogel Barriers," Obstetrics and Gynecology, 83(1): 59 (1994).

(Continued)

*Primary Examiner*—Jon P Weber
*Assistant Examiner*—Abdel A Mohamed
(74) *Attorney, Agent, or Firm*—Dardi & Associates, PLLC

(57) ABSTRACT

Some aspects of this disclosure relate to a method for crosslinking a biological fluid comprising combining a biological fluid with a crosslinker to covalently crosslink proteins endogenous to the biological fluid to form a crosslinked gel. Examples of a biological fluid are blood, plasma, or serum.

12 Claims, 7 Drawing Sheets

U.S. PATENT DOCUMENTS

| | | | |
|---|---|---|---|
| 6,371,975 | B2 | 4/2002 | Cruise et al. |
| 6,379,373 | B1 | 4/2002 | Sawhney et al. |
| 6,410,645 | B1 | 6/2002 | Pathak et al. |
| 6,458,147 | B1 | 10/2002 | Cruise et al. |
| 6,458,889 | B1 | 10/2002 | Trollsas et al. |
| 6,465,001 | B1 | 10/2002 | Hubbell et al. |
| 6,566,406 | B1 * | 5/2003 | Pathak et al. ............ 514/772.1 |
| 6,596,471 | B2 | 7/2003 | Pathak et al. |
| 6,632,457 | B1 | 10/2003 | Sawhney |
| 6,639,014 | B2 | 10/2003 | Pathak et al. |
| 6,673,093 | B1 | 1/2004 | Sawhney |
| 6,673,851 | B2 * | 1/2004 | Moy et al. ................ 522/173 |
| 6,800,080 | B1 | 10/2004 | Bates |
| 6,815,212 | B2 | 11/2004 | Ness et al. |
| 6,818,018 | B1 | 11/2004 | Sawhney |
| 6,846,851 | B2 | 1/2005 | Nakhmanovich et al. |
| 6,875,193 | B1 | 4/2005 | Bonnette et al. |
| 6,911,227 | B2 | 6/2005 | Hubbell et al. |
| 6,923,986 | B2 | 8/2005 | Pathak et al. |
| 6,958,212 | B1 * | 10/2005 | Hubbell et al. ................ 435/6 |
| 7,009,034 | B2 | 3/2006 | Pathak et al. |
| 7,153,519 | B2 | 12/2006 | Hubbell et al. |
| 2002/0111532 | A1 | 8/2002 | Pathak et al. |
| 2002/0119563 | A1 | 8/2002 | Pathak et al. |
| 2007/0254005 | A1 | 11/2007 | Pathak et al. |
| 2007/0282366 | A1 | 12/2007 | Khosravi et al. |

FOREIGN PATENT DOCUMENTS

| | | |
|---|---|---|
| WO | 9109641 A1 | 7/1991 |
| WO | 9603159 A1 | 2/1996 |
| WO | 9835631 A1 | 8/1998 |
| WO | 9934833 A1 | 1/1999 |
| WO | 9914259 A1 | 3/1999 |
| WO | 9922770 A1 | 5/1999 |
| WO | 2006031358 A2 | 3/2006 |
| WO | 2007001926 A2 | 1/2007 |

OTHER PUBLICATIONS

Sawhney, et al., "Bioerodible Hydrogels Based on Photopolymerized Poly(ethylene glycol)-co-poly($\alpha$-hydroxy acid) Diacrylate Macromers," Macromolecules, 26:581-587 (1993).

Sawhney et al., "Optimization of Photopolymerized Bioerodible Hydrogel Properties for Adhesion Prevention", Journal of Biomedical Materials Research, 28:831-838 (1994).

Schlag et al., "Fribin Sealant in Orthopedic Surgery" Fibrin Sealant in Operative Orthopedic Surgery, vol. 1-7:269-284 (1986).

* cited by examiner

PROTEIN CROSSLINKERS, CROSSLINKING METHODS AND APPLICATIONS THEREOF

CROSS-REFERENCE TO RELATED APPLICATIONS

This application claims priority to provisional patent application 60/794,384 filed Apr. 24, 2006 which is hereby incorporated herein by reference.

TECHNICAL FIELD

The technical field, in general, includes biomaterials made from biological fluids as well as new protein crosslinkers and crosslinking methods for crosslinking biomolecules in the fluids.

BACKGROUND OF THE INVENTION

A surgical adhesive can have several biomedical applications. For instance, a surgical adhesive can be used as a replacement of suture, as a surgical sealant to prevent air and fluid leaks, or as a drug delivery reservoir for the delivery of bioactive compound. The primary function of surgical adhesives to hold two pieces of tissues together with a strong adhesive bond, which will last through the healing process. After the healing process, the adhesive will ideally disintegrate into nontoxic products, which are then eliminated from the body. A surgical adhesive should ideally have good handling properties, set up quickly in moist environment with adequate bond strength. In addition it should be nontoxic, biocompatible and biodegradable.

Many different types of tissue adhesives have been reported in the medical and materials literature. Cynoacrylates and fibrin based adhesive systems have been useful. Cynoacrylate based adhesives are excellent tissue adhesives but the toxicity of cynoacrylate monomer and concern over its toxic degradation products has effectively prevented it from getting regulatory approval.

Fibrin glue is a biological adhesive derived from human or animal blood. Fibrin based adhesives are commercially available in Europe under the trade name TISSUCOL® and TISSEL® and have been recently approved for use in USA. Typical commercial fibrin glue kit consists of a vial of lyophilized concentrated pooled blood human fibrinogen that also contains fibronectin, Factor XIII and reduced amounts of plasminogen. The concentrate is reconstituted with a reconstituting solution and warmed to 37° C. The second component of the adhesive system is a lyophilized bovine thrombin solution, which is also reconstituted with calcium chloride solution. The formulation may also contain additional components like fibrionolysis inhibitor. The reconstituted solutions are mixed and used as a surgical adhesive system. Fibrin adhesives have been demonstrated to be nontoxic, biocompatible and bioresorbable.

The mechanism of fibrin glue involves last stages of coagulation cascade, in which fibrinogen is converted to fibrin in presence of thrombin, Factor XIII, fibronectin and ionized calcium (Ca+2). The speed of this coagulation process depends on the thrombin concentration used and may be varied according to the need. The resultant fibrin clot or gel is primarily held up by electrostatic and hydrogen bonding and is susceptible to rapid dissolution by proteolytic enzymes such as plasmin. Factor XIII via transamination introduces the covalent crosslinks, which makes the fibrin clot resistant to proteolytic degradation. It also improves the mechanical properties of fibrin glue.

Fibrinogen is the third largest abundant protein component of blood plasma and is perhaps most important component of fibrin adhesive formulation. Fibrinogen is the third largest abundant protein component of blood plasma and is perhaps most important component of fibrin adhesive formulation. A second important protein is Factor XIII whose concentration is 0.015 mg/ml and has a molecular weight 320 KD. In order to have good adhesive properties and fast gelation times, a higher concentration of fibrinogen is desired in a coagulable protein concentrate. The strength of adhesive bond formed is directly proportional to concentration of fibrinogen in the formulation and method of its preparation. Cryoprecipitation is the most common method used in preparation of coagulable protein concentrate. This method involves a) freezing a fresh blood plasma which has been screened for hepatitis or AIDS at 80° C. for at least 6 hours preferably for at least 12 h. b) raising the temperature of frozen plasma to around 0-4° C. so as to form a supernatant and a cryoprecipitated suspension containing fibrinogen and Factor XIII and c) recovering the cryoprecipitated suspension by decanting the supernatant. Another method described in the patent and medical literature is the use of common low toxic organic/inorganic compounds such as ethanol, polyethylene glycol, poly(vinyl alcohol), 1-6-hexanoic acid, ammonium sulfate and glycerol.

Most of the methods reported in the literature have one common feature, which is isolation by phase separation or precipitation step. All the precipitation approaches suggested for the preparation of the fibrinogen-containing fraction for this purpose are too time consuming and complex to be finished in a short time period to be accomplished during the course of the surgery. Also in some approaches such as cryoprecipitation, special equipment like refrigerated centrifuges are required. Different methods of precipitations produce fractions with different adhesive characteristics. Also different methods of precipitation produce precipitates of different particle size. Some finer particle sizes are difficult to separate from supernatant liquids, which may result into poor yield of final protein concentrate. Many times multiple precipitation and redissolution steps are required to achieve desirable concentrations. Many methods rely on preparation in an open test tube systems. These open test tube products are often stored for extended periods of time in refrigerator and methods that may not meet the requirements of the American Association of Blood Banks for open-system storage of blood products. Phase separation by precipitation may also denature the protein and alter its natural conformation. Many enzymatic reactions are sensitive to protein conformation. Isolation by precipitation may also affect the yield of final product. Many times up 10-20% coagulable protein is lost in such processes.

The bovine thrombin used in commercial and autologus fibrin adhesive formulation may carry bovine spongioform encephalitis (BSE, responsible for mad cow disease) and other viruses pathogenic to humans. Also, bovine thrombin is a potent antigen, which can cause immunological reactions in humans. Thus, the use of bovine thrombin involves the potential risks to the patient.

The fibrin clot formed using commercial fibrin glue formulations is degraded by the proteolytic enzymes found inside the human body. The current formulations do not provide any control over its degradation.

SUMMARY OF THE INVENTION

Some embodiments are an improved sealant that uses natural biological fluid to make an adhesive crosslinked gel. Thus some aspects of the invention relate to a method for crosslinking a biological fluid by combining a biological fluid with a crosslinker to covalently crosslink proteins endogenous to the biological fluid to form a crosslinked gel. Some embodiments employ a liquid crosslinker having a molecular weight of no more than about 2000. The crosslinker may be essentially free of water before combining the crosslinker with the biological fluid and may, e.g., have a polyethylene glycol derivative, a hydrolytically degradable group, be a solid at room temperature, or require melting the crosslinker prior to combining the crosslinker with the fluid.

Some embodiments relate to low molecular weight precursor comprising a liquid crosslinker with a molecular weight of no more than about 2000 or 4000 that comprises at least about 3, 5, or 8 functional groups that are strong electrophiles. Such a crosslinker may be prepared in some embodiments as a melt at about 10° C. to about 50° C. The crosslinker may be, e.g., a polyethylene glycol derivative or consists essentially of a polyethylene glycol in which each of at least three end groups has been replaced with one of the functional groups. Examples of functional groups are epoxide, N-hydroxysuccinimide, acrylate, methacrylate, maleimide, or N-hydroxysulfosuccinimide.

Some embodiments relate to a method for forming a biomaterial in situ comprising combining a precursor with a solution of a crosslinker in an organic solvent to covalently crosslink the precursor to form a crosslinked gel. For instance, the precursor may be dispersed (solubilized) or dissolved in the organic solvent and the organic solvent is miscible with water. The organic solvent may be a small molecule, e.g., dimethyleformamide or dimethyl sulfoxide or a polymer, e.g., methoxy PEG or propylene glycol.

Some embodiments relate to a water soluble crosslinker comprising a purified preparation essentially free of water comprising a molecule that comprises a formula of R-(A)n wherein A is a strong electrophilic functional group, n is at least 2, and R has a molecular weight of about 40 to about 4000 and comprises an amide, secondary amine, or tertiary amine functional group.

Some embodiments relate to a method of forming a biological material in a blood vessel with a lumen defined by walls of the blood vessel comprising combining a biological fluid with a crosslinker to covalently crosslink proteins endogenous to the biological fluid to form a crosslinked gel in situ on the walls of the blood vessel. Such a gel may contain a therapeutic agent such as a marker, radio-opaque marker, dye for visualizing in the light spectrum recognized by the human eye, a drug, or a nucleic acid. The nucleic acid may comprise, e.g., an antisense, RNAi, RNA, DNA, gene, a sequence encoding a polypeptide, or a messenger RNA.

Some embodiments relate to a biomaterial for drug delivery comprising a gel that comprises proteins covalently crosslinked with a synthetic crosslinker that is conformed to a wall of a blood vessel. Examples of the protein are a blood fluid protein, fibrin, fibrinogen, or albumin.

DETAILED DESCRIPTION OF THE INVENTION

Figure 1:
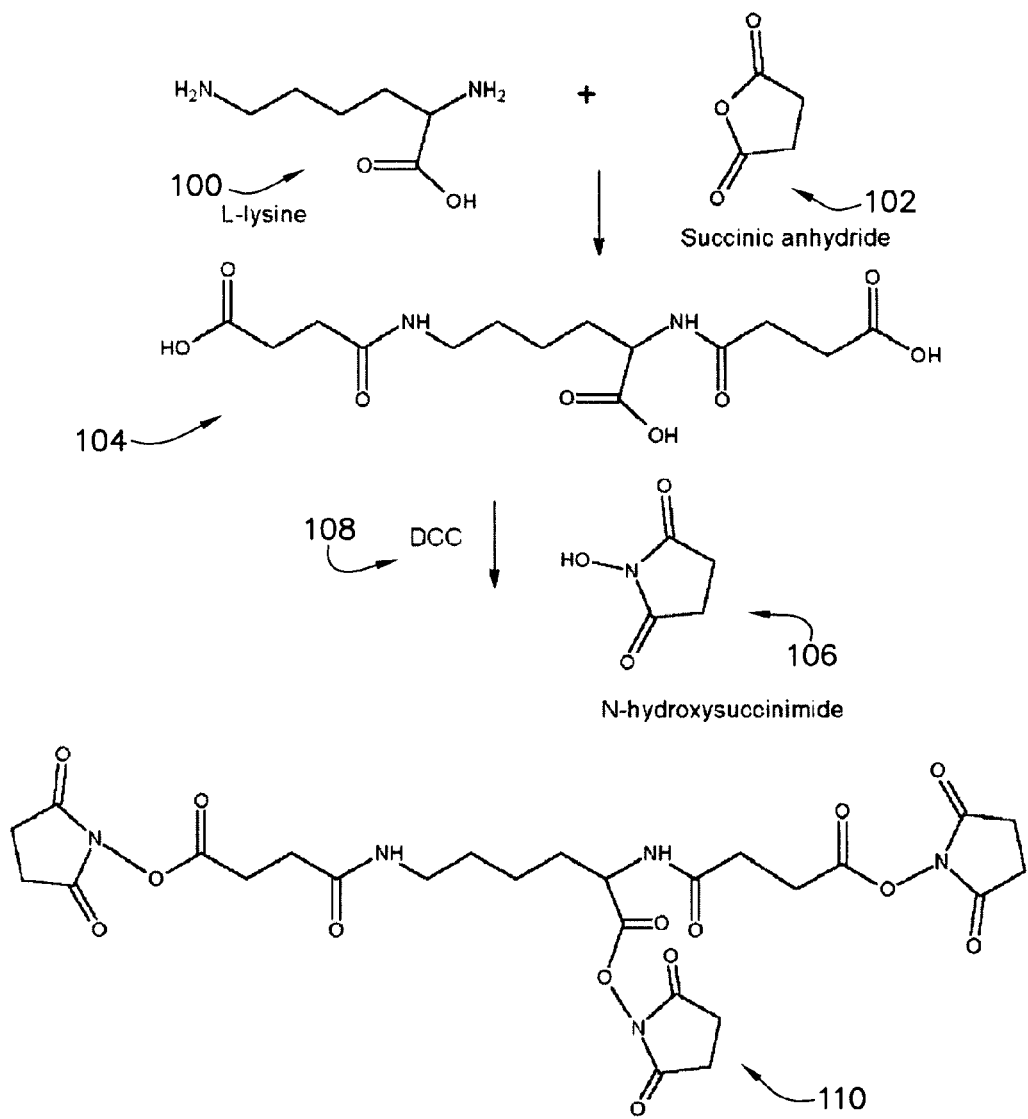
FIG. 1 depicts a synthesis scheme for water soluble aminoacid based crosslinker prepared from L-lysine.

Despite of its commercial use in Europe and other countries in the world, fibrin glue is not used extensively due to viral contamination of blood born virus such as AIDS and hepatitis B. This situation has lead to the development single donor and patient autologous fibrin adhesive formulations. This method reduces or eliminates the risk of blood born viral diseases contamination; however, the methods used to prepare autologous adhesive are viewed as time consuming, cumbersome and unpredictable. This resulted into a clinical need for effective surgical adhesive, which is safe, commercially available and efficacious.

Accordingly, there is a need for a fibrin sealant that can be delivered to a patent without the risk of viral contamination or other side effects. Also there is need for simple crosslinking mechanism, which will eliminate or reduce amount of handling required to prepare fibrin glue and its dependence on a clotting factors and calcium ion concentration. In many surgical applications, especially, in many controlled drug delivery applications, a control over degradation of fibrin clot is highly desirable, but there is little control over fibrin glue degradation rates. Accordingly, there is also a need for controlling the degradation of the crosslinked fibrinogen gels.

Set forth herein are new methods to clot blood or blood derived proteins using water soluble crosslinkers. The natural clotting process is quite complex and requires a number of steps and components/chemical that can take several hours to complete. The use of these crosslinkers, however, avoids the natural clotting process and forms a clot by crosslinking the proteins present in the blood. Further, a biological fluid derived from a mammalian source can be converted into chemically crosslinked network with minimum manipulation. Human blood or blood derived fluids may be easily isolated in a sterile manner and mixed with a crosslinking agent capable of reacting with functional groups available on the components of biological fluid. The resultant crosslinked network or clot is useful for a variety of surgical and medical applications.

Biological Fluid Compositions for Reaction with Crosslinkers

A biological fluid derived from blood or a blood fluid may be used for reaction with crosslinkers. The blood may be derived from, e.g., a mammalian source, where suitable sources include cows, sheep, pigs, deer, humans or other mammals. Blood is a highly specialized circulating tissue consisting of several types of cells suspended in a fluid medium known as plasma. The cellular constituents are: red blood cells (erythrocytes), which carry respiratory gases and give it its red color because they contain hemoglobin (an iron-containing protein that binds oxygen in the lungs and transports it to tissues in the body), white blood cells (leukocytes), which fight disease, and platelets (thrombocytes) which are cell fragments that play an important part in the clotting of blood. Whole blood is blood that has not been modified except for the addition of an anticoagulant. Plasma contains some clotting factors and other proteins, e.g., albumin and antibodies. Once plasma is separated from the red blood cells, it can be frozen and kept for up to a year until it is needed. Once thawed, it is called fresh frozen plasma. Plasma differs from serum in that plasma contains fibrin and other soluble clotting elements.

A biological fluid comprising serum may be used for reaction with crosslinkers. The term serum refers to the fluid obtained upon separating whole blood into its solid and liquid components after it has been allowed to clot. Serum advantageously has a multitude of factors that enhance cellular activities and is commonly used in the cell culture arts for that reason. Serum may be prepared autologously, from pooled sources, or from human or animal sources. Serum may be made in preparation for a medical procedure, e.g., immediately before or during the same, and used with a crosslinker. The term crosslinking refers to forming covalent bonds or crosslinks between polymers, e.g., linear polymers, branched polymers, dendrimers, or a macromolecular molecules. The term crosslinker refers to a compound capable of forming crosslinks in such a context.

Blood fluid is a term that refers to whole blood or proteinaceous fluid derived from whole blood having endogenous blood proteins that have remained in the fluid without being precipitated or isolated from the whole blood. One advantage of avoiding the use of previously isolated proteins is that skipping the isolation saves time and simplifies procedures. Avoiding protein isolation/reconstitution steps can also help to preserve protein structure by minimizing denaturation or introduction of impurities. Endogenous refers to a material that is native to the system, meaning that it is typically found therein. Thus blood has endogenous proteins that are present in the blood. Exogenous materials are those that are later introduced. Thus hyaluronic acid added to blood would be exogenous. The addition of extra fibrinogen to blood would thus be the addition of an exogenous native protein.

Thus serum and plasma (including fresh frozen plasma) are blood fluids. Blood fluids can also be whole blood that has been treated to selectively remove some components, e.g., by filtering, clotting, or immuno-isolation, or with the red blood cells removed. Blood fluid may also include components that have been added, e.g., proteins, drugs, anticoagulants, or antibodies. Significantly, processes for creating gels from conventional protein solutions may not work when applied to gelation of a blood fluid. Many blood fluids contain a plurality of protein types, e.g., two, three, four, or more types. The term type refers to chemically distinct species that are essentially not derivatives of each other; thus albumin and immunoglobulin are two types of proteins. A blood-derived product, prior to use, may be screened for the presence of one more pathogens, e.g., AIDS, Hepatitis B, or other infectious diseases. Autologous or pooled sources may be used. Embodiments for reaction with crosslinkers include blood derived materials such as autologous or single donor blood plasma, or a fibrinogen component of commercial fibrin glue adhesive system.

In addition, compositions may be supplemented with additional materials capable of reacting with the crosslinker, e.g., to form covalent bonds. For instance, proteins may be added, e.g., the human proteins albumin, fibrinogen; polylysine; polyaminoacids, derivatives thereof (e.g., fibrin monomer or enzymatically hydrolyzed fibrinogen) or synthetic polymers, e.g., a hydrophilic polymer, polyalkylene oxide (e.g., polyethylene oxide or polypropylene oxide or their copolymers), or amine terminated polyethylene glycol. Additional agents which may added to the composition include: proteins associated with coagulation, e.g., Factor II, fibronectin; viscosity modifiers, such as collagen, sodium hyaluronate, polysaccharides; antioxidants, e.g., hydroquinone, vitamin E, vitamin C; buffering agents, e.g., HEPES, sodium borate, phosphates; and others, e.g., processing aids, antifibrinolytic agents, platelet activating agents, or wound healing agents. Also, a visualization agent may be included. Visualization agents (i.e., agents that may help a surgeon see with the naked eye those tissues to which the fibrin glue or other sealants or adhesives have been applied) include blood compatible chromogenic dyes, where specific visualization agents of interest are those that provide for color contrast with the background tissue, with blue and green being preferred colors, where specific agents include: indocyanine green, methylene blue, FD& C no. 1, FD & C no. 6, eosin, fluorescein, and the like. Fluorescence compounds may be used at concentrations visible to the naked eye, e.g., non-toxic fluorescent compounds, fluroescein. Further, fluorescent visualization agents may be used for visualization of fluorescence using a suitable light source or imaging techniques.

Other biological fluids or compositions may be reacted with crosslinkers as described herein. Biological fluids may be of natural or synthetic origin. The term native biological fluid refers to a fluid located within or produced by an organism. The biological derived fluid or other composition may be any aqueous composition that comprises one or more proteins of interest. Such compositions may be naturally occurring compositions, e.g., physiologically derived fluids, blood, plasma, serum, urine, cerebrospinal fluid, tears, saliva, milk, mucus, peritoneal cavity fluid. Such compositions may be synthetically prepared compositions, e.g., tissue culture medium, tissue culture medium containing recombinant proteins, synthetic polymers, polymers with functional groups found on proteins such as amines, sulfhydryl, carboxyls, or hydroxyls, amine-terminated polyethylene glycol, amine-terminated polyethers, JEFFAMINE™, or mixtures of thereof. Examples of proteins are, e.g., albumin, fibrinogen, fibrin, collagen, fibronectin, and laminin. Biological fluids may be obtained from a variety of hosts, e.g., cows, sheep, pigs, deer, or humans. For example, the subject methods can be used to produce enriched protein compositions from cow or sheep milk, where the cow or sheep may be a transgenic animal engineered to produce milk containing a recombinant protein of interest.

A biological fluid composition may be used immediately upon collection or stored for use at a later time. Any suitable storage means may be employed. The storage means may be sterile where the composition is to ultimately be used in a physiological setting, e.g., where it is to be used in a drug delivery vehicle, or as a surgical adhesive. One technique of storing the composition is to lyophilize the composition and package the lyophilized product in a sterile packaging for subsequent use, e.g., in a syringe. Alternatively, the composition may be stored at a reduced temperature, e.g., from about 4 to −20° C. or lower.

Preparation of the biological fluid may be performed at both the laboratory scale or scaled-up. For instance, a large volume of fibrinogen rich composition may be prepared, e.g., from pooled plasma. Or, for example, whole blood may be withdrawn from a mammalian host into a sterile syringe containing an anticoagulant. The cellular materials such as red blood cells may be separated with conventional protocols, and methods are available for preserving the composition's sterility. Small-scale processes are convenient to prepare an autologous tissue adhesive, e.g., where the adhesive is prepared from a patient's own blood prior to, or during, a surgical operation. For scale-up preparations from large volumes of initial blood composition, pooled blood plasma, which may be screened for viruses such as Hepatitis B, and AIDS, may be transferred to and packaged in a sterile fashion. In some embodiments, the biological fluid is taken from the patient no more than about 12 hours or 24 hours before the gel is formed. Alternatively the fluid may be taken in advance and stored until needed, for instance by freezing or refrigeration.

Crosslinkers

A multifunctional crosslinker may be reacted with a biological fluid to form a gel. The term multifunctional refers to crosslinkers with at least two reactive functional groups for forming covalent bonds. Crosslinkers may include, for example, 2, 3, 4, 5, 6, 7, 8, 9, 10, 11, or 12 functional groups, or more. The crosslinkers include those that are a liquid at a temperature of about 10° C. to about 50° C.; artisans will immediately appreciate that all the ranges and values within the explicitly stated ranges are contemplated. Thus crosslinkers are included that are liquid at room temperature (about 20° C.) or at physiological temperature (about 35° to about 40° C.). The crosslinkers also may include low molecular weight water soluble crosslinkers with functional groups reactable with materials in the biological composition to form a covalent bond.

The functional groups may be, e.g., electrophiles reactable with nucleophiles, groups reactable with specific nucleophiles, e.g., primary amines, groups that form amide bonds with materials in the biological fluids, groups that form amide bonds with carboxyls, activated-acid functional groups, or a combination of the same. The functional groups may be, e.g., a strong electrophilic functional group, meaning an electrophilic functional group that effectively forms a covalent bond with a primary amine in aqueous solution at pH 9.0 and/or an electrophilic group that reacts by a of Michael-type reaction. The strong electrophile may be of a type that does not participate in a Michaels-type reaction or of a type that participates in a Michaels-type reaction.

A Michael-type reaction refers to the 1,4 addition reaction of a nucleophile on a conjugate unsaturated system. The addition mechanism could be purely polar, or proceed through a radical-like intermediate state(s); Lewis acids or appropriately designed hydrogen bonding species can act as catalysts. The term conjugation can refer both to alternation of carbon-carbon, carbon-heteroatom or heteroatom-heteroatom multiple bonds with single bonds, or to the linking of a functional group to a macromolecule, such as a synthetic polymer or a protein. Michael-type reactions are discussed in detail in U.S. Pat. No. 6,958,212, which is hereby incorporated by reference for all purposes to the extent it does not contradict what is explicitly disclosed herein.

Examples of strong electrophiles that do not participate in a Michaels-type reaction are: succinimides, succinimidyl esters, NHS-esters, or maleimides. Examples of Michael-type electrophiles are acrylates, methacrylates, methylmethacrylates, and other unsaturated polymerizable groups.

Some conventional approaches rely on PEGs to create a water soluble crosslinker (e.g., as in U.S. Pat. No. 5,874,500). While such materials can be useful, and may be used herein as appropriate, the use of non-PEGs can give rise to crosslinked compositions with different physical properties. Crosslinkers that are non-polyethylene glycol (PEG, a polymer with ($CH_2$—$CH_2$—O) repeats, this mer also being referred to as the PEG group) based compounds are included. Some crosslinkers are free of the PEG group ($CH_2$—$CH_2$—O), some are free of more than one PEG group, and some are free of all ethers. Other crosslinkers have more than one PEG group but do not have more than two of them adjacent to each other. Some crosslinkers have less than 500, 400, 300, 200, 100, or 50 in molecular weight of PEG groups, while others have between 40-500 molecular weight of PEG groups; artisans will immediately appreciate that all the ranges and values within the explicitly stated ranges are contemplated.

Crosslinkers may be prepared in a purified preparation that has a high concentration of the crosslinker, i.e., more than about 75% w/w. Such preparations may be prepared with a greater purity, e.g., more than about 90%, 95%, or 99% w/w. More than one type of crosslinker may be mixed to together to form the purified preparation as appropriate. One advantage of using such a preparation is that it may be used directly without dilution, e.g., when crosslinking other precursors.

Some crosslinker preparations may be prepared to be essentially free of water. For instance, dry reagents may be used, or the crosslinker may be purified through precipitation or lyophilization processes.

Liquid Crosslinkers

Some crosslinkers may be liquid or semisolid in the about 10° C. to about 50° C. temperature range. Liquid crosslinkers can form melts, meaning that they are liquid without the addition of other liquids. Liquids or melts have some advantages as compared to aqueous solutions of crosslinkers. Melts can be used without dilution. Liquids can be reacted directly with a material, e.g., a biological fluid, protein, or fibrinogen rich solution without dilution. Liquids can be easily transported through minimally invasive surgical tools to a surgical site. Liquids are often relatively quicker and easier to dissolve in water because they do not have to overcome crystallization energy, which is normally associated with crystalline solids. In aqueous solutions, some functional groups, e.g., n-hydroxysuccinimide esters, undergo unwanted hydrolysis, especially at higher pH of more than about 7.5 pH. An organic medium such as a melt is free of water, does not have such side reactions, and can be more stable in storage and use.

One embodiment of a crosslinker is a low molecular weight polyethylene glycol derivative with a terminal protein reactive group such as epoxide, n-hydroxysuccinimide or n-hydroxysulfosuccinimide group. The term protein-reactive refers to an electrophilic group that forms a covalent bond with a nucleophile that is an amine, sulfhydryl, or hydroxyl or is a nucleophile that reacts with a carboxyl or hydroxy. The protein-reactive functional group is thus part of an electrophilic-nucleophilic reaction scheme, which is a term customary to these arts. The protein-reactive group may be a strong electrophile. The molecular weight range for the low molecular weight polyethylene glycol derivative is from about 100 to about 2000 (either number-averaged or weight-averaged); artisans will immediately appreciate that all the ranges and values within the explicitly stated ranges are contemplated. A polyethylene glycol derivative has at least three adjacent PEG repeats. N-hydroxysuccinimide esters, among other functional groups, may be used to form amide linkages with amine groups under physiological conditions. A PEG end group refers to the last group in a chain, i.e., a hydroxyl unless the PEG has been modified; accordingly, a linear PEG has two ends groups and a tetrameric PEG has four end groups.

One embodiment of a synthetic liquid crosslinker has a plurality of PEG groups, is a liquid at room temperature, and has a plurality of protein-reactive functional groups. For instance, polyethylene glycol 600 diacid (Fluka, catalog 81324) is reacted with n-hydroxysuccinimide in presence of N,N-dicyclohexylcarbodiimide to obtain a N-hydroxysuccinimide ester of polyethylene glycol 600 diacid (PEGNHS). This liquid crosslinker is capable of crosslinking proteins, has two N-hydroxysuccinimide esters and is liquid at approximately room temperature.

Another embodiment of a synthetic liquid crosslinker has a branched structure and a degradable group. For instance, a 3 arm polyethylene glycol is first reacted with glutaric anhydride in presence pyridine. The terminal carboxyl group of this polyethylene glycol ester is then reacted with n-hydroxysuccinimide to form a terminal n-hydroxysuccinimide (NHS) ester. The glutarate ester serves as degradable link in the liquid crosslinker. In another embodiment, poly(vinyl pyrrolidinone-co-acrylic acid) copolymer, average molecular weight 20000 Daltons (Aldrich, Catalog number 41,852-8) and is reacted with n-hydroxysuccinimide in presence of N,N-dicyclohexylcarbodiimide to obtain a N-hydroxysuccinimide ester of poly(vinyl pyrrolidinone-co-acrylic acid) copolymer. The resultant product is a semi-viscous liquid. In another embodiment, N-hydroxysuccinimide ester of 1,2,3,4-butanedicarboxylic acid (BTANHS) was synthesized. Briefly, 1,2,3,4-butanedicarboxylic acid and n-hydroxysuccinimide were reacted using DCC as a catalyst. This crosslinker has 4 protein reactive n-hydroxysuccinimide groups. The liquid crosslinkers may contain degradable linkages.

In some embodiments, compositions are made having a mixture of crosslinker types, e.g., a blend. For instance, a composition of crosslinkers is made by blending/mixing two or more crosslinkers, one of which is a liquid at about 10° C. to about 50° C. For instance, a liquid crosslinker made PEG 600 diacid is mixed with 4 arm-n-hydroxysuccinimide ester of polyethylene glycol carboxymethylene-butyric acid, average molecular weight 10000 Daltons (Nektar Therapeutics (formerly Shearwater) 4 arm CM-HBA-NS-10K).

In some embodiments, liquid crosslinkers are used without reconstitution in other media such as water, solvents, and/or other precursors. Thus the liquid crosslinkers may be essentially free of water. Or the crosslinkers may be free of all aqueous and organic solvents. Or the crosslinkers may be free of water but mixed with biocompatible solvents or organic solvents. Some in situ materials formation processes may be particularly advantageous with one or more of these features, e.g., the polymerization or crosslinking of sealants or dressings in a patient.

A category related to liquid crosslinkers is dispersible crosslinkers. Some crosslinkers are dispersible, meaning that they are not truly liquids or solvated in the solvent as used, but are nonetheless effectively miscible in a solvent. Dispersible is a term of art, e.g., as used in U.S. Pat. Nos. 6,326,419 and 6,846,851, each of which are hereby incorporated by reference to the extent they do not contradict what is explicitly disclosed herein.

Crosslinker Solvents

The crosslinkers may be used with conventional solvents. And non-conventional solvents may also be used, specifically non-aqueous water soluble biocompatible, non-reactive solvents. The may be used for the various types of crosslinkers, including crosslinkers that are liquid or solid at about 10° C. to about 50° C. Conventional approaches to in-situ polymerization have focused on use of aqueous precursors that polymerize with each other at the site of use in the patient. Aqueous precursors and aqueous solvents are conventionally regarded as being highly biocompatible. What is not conventionally appreciated, however, is that some organic solvents are also biocompatible. The reduction or elimination of water can improve storage life and stability of crosslinker or other precursors. Further, eliminating water can advantageously eliminate a step of dissolving a crosslinker or other precursor in water. For instance, crosslinkers may be dissolved in non-aqueous solvents and be liquids that are ready for use as-is, and without the addition of solvents or reaction aids.

One group of non-conventional solvents are polymers wherein the functionalities are stable groups in the presence of a strong electrophile or nucleophile. For the sake of clarity, the term stable group refers to a functional group that (a) does not undergo substantial decomposition in water at pH 4-11 or in dimethylsulfoxide and (b) substantially does not react in one hour with an n-hydroxysuccinimide ester in water or in dimethyleformamide at pH 9.0 to form a covalent bond and that (c) substantially does not react in one hour with a primary amine at pH 4.0 to 11.0 to form a covalent bond. The phrase "substantially does not react" refers to a reaction of less than 3% of the available stable functional groups. Decomposition refers to a spontaneous chemical rearrangement of the group upon being dissolved in the solvent. Functional groups (sometimes called "groups" or moieties) are specific collections of atoms within molecules that are responsible for the characteristic chemical reactions of those molecules. The same functional group will undergo essentially the same or similar chemical reaction(s) regardless of the size of the molecule it is a part of. The following groups are not stable functional groups: primary amines, primary sulfhydryls, hydroxyls, carboxyls, aldehydes, cyanates, isocyanates, haloalkanes, and peroxides.

One set of such solvent-polymers are polyethylene glycol derivatives that have been treated to replace their hydroxyl functional groups with a stable group. In some embodiments, these are used as a solvent for polyethylene glycol based crosslinkers. In some embodiments, the polyethylene glycol hydroxyls are converted to methyl ether groups. Hydroxy functional groups of polyethylene glycol may also blocked with various other functional groups, for example, hydroxy groups may be reacted with acetic anhydride to form an acetate blocked polyethylene glycol. Polyethylene glycol based solvents are advantageously water soluble and non-toxic. Examples of polyethylene glycol solvents with stable groups are: polyethylene glycol methyl ether and polyethylene glycol monomethyl ether. Exemplary molecular weights are 200 to 2000; artisans will immediately appreciate that all the ranges and values within the explicitly stated ranges are contemplated.

By way of example, polyethylene glycol dimethyl ether, molecular weight 400 (Sigma/Aldrich Product Number: 81311) is dried at 120 under vacuum for 24 h to remove traces of moisture which may react with the crosslinker. 4 arm-n-hydroxysuccinimide ester of polyethylene glycol carboxymethylene-butyric acid, average molecular weight 10000 Daltons (Shearwater 4 arm CM-HBA-NS-10K) is dissolved in dry polyethylene glycol dimethyl ether, molecular weight 400 to form, e.g., 1 to 40% solution. The solution is filter sterilized and is used in crosslinking reactions. Polyethylene glycol dimethyl ether serves as a polymeric non-reactive, non-toxic, water soluble solvent for, e.g., an NHS ester functional group.

An organic water soluble solvent that is suitably biocompatible may also be used with a crosslinker or other precursor as appropriate. Dimethyl sulfoxide (DMSO) is one such solvent. Dimethyleformamide (DMF) and n-methyl pyrrolidinone (NMP) are also biocompatible in suitable amounts, as are methoxy PEGs, propylene glycols, and ethanol. Fatty acids, such as, oleic acids is another class of organic solvent. Vitamin E or its derivatives are another class of liquids which may be used. It is understood that the choice of solvent will depend on functional groups used in crosslinking and solubility in the solvent.

By way of example, dry NMP may be used to dissolve a 4 arm-n-hydroxysuccinimide ester of polyethylene glycol carboxymethylene-butyric acid, average molecular weight 10000 Daltons (Nektar Therapeutics, 4 arm CM-HBA-NS-10K) to form, e.g., a 1-40% solution. The solution is filter sterilized using 0.2 micron Teflon filter and is used in crosslinking reactions with polyfunctional amines such as amine terminated polyethylene glycol or trilysine. The amine and NHS ester may have molar equivalent concentrations for efficient polymerization and crosslinking. The reaction can be carried out "in situ" using a minimally invasive surgical technique. Aprotic solvents like n-methyl pyrrolidinone, dimethyl sulfoxide are preferred due to their proven safety and water solubility and high solvating power. Other solvents that may be used are ethanol, isopropanol, 1,2-propane diol, 1,4-butane diol, or ethyl lactate.

Water Soluble Crosslinkers

New water soluble low molecular weight based crosslinkers are also disclosed herein. Conventionally, sulfonation is used to make low molecular weight crosslinkers water soluble. For instance, many n-hydroxysuccinimide derivatives are insoluble in water. For example, a commercially available n-hydroxysuccinimide (NHS) of glutaric acid or suberic acid is insoluble in water. This restricts the use of many NHS esters compounds in aqueous environments. For instance, a sulfonated derivative of n-hydroxysuccinimide, commonly referred as sulfoNHS, has been reported. The sulfonate group maintains the reactivity of the NHS functional group toward amine groups and makes the NHS derivative water soluble. However, sulfoNHS derivatives are expensive and require the use of multiple steps to achieve their synthesis. NHS-based crosslinkers are described herein, however, that are simple to make and do not use the sulfoNHS groups to achieve water solubility.

Some embodiments of the water soluble crosslinkers are represented by the formula R-(A)n (Formula I) or A-R-A (Formula II). A represents an activatable functional group, e.g., n-hydroxysuccinimide. N represents the number of A functional groups and is at least two. R represents a molecule with a molecular weight of about 40 to about 4000. R contains at least two groups W. W represents a water-soluble group capable of forming hydrogen bonds with water but not capable of reacting with activated acid under normal storage conditions, e.g., amide, secondary amine, or tertiary amine functional groups. R may be a polymer or a non-polymer, e.g., an alkyl or alkoxy. In some embodiments, A represents a strong electrophilic functional group, meaning an electrophilic functional group that effectively forms a covalent bond with a primary amine in aqueous solution at pH 9.0 and/or an electrophilic group that reacts by a of Michael-type reaction. Alternatively, A may be a strong electrophile that excludes a Michaels-type reaction or an electrophile that participates in a Michaels-type reaction.

Exemplary compositions and synthesis schemes are given in FIGS. 1 to 5. For instance, aliphatic diamines such as ethylene diamine may be reacted with succinic anhydride. The acid groups thereby formed may be activated using n-hydroxysuccinimide groups. Many diamines may be used in place of ethylene diamine these include but not limited to are: 1,3-propyldiamine, 1,4-butanediamine, 1,6-hexanediamine, polypropylenimine tetraamine dendrimer, or multibranched dendrimers. The schemes below illustrate diamine reactions; multi-amines, however, may be reacted using the same processes. Thus molecules with at least 3 functional groups may be reacted to make crosslinkers or other precursors, e.g., 3-16 functional groups, or more, e.g., as with dendrimers; artisans will immediately appreciate that all ranges and values between the explicitly stated values are contemplated, e.g., 3, 4, 6, 8, 10, 12.

FIG. 1 is synthesis Scheme I for water soluble amino acid based crosslinker prepared from L-lysine. Lysine 100 is first reacted with excess of succinic anhydride 102 to form an acid terminated amide derivative 104. The acid groups of the acid amide are activated by forming n-hydroxysuccinimide ester 106 with 1,3-dicyclohexyl carbodiimide (108, DCC) as a catalyst to form product 110, which is a water soluble low molecular weight crosslinker of general formula A-R-A, with the amide groups being the W functional groups of R. The trifunctional NHS derivative is soluble in water due to presence of two amide groups in the molecule. The solubility could be further enhanced by forming quaternary compounds of nitrogen molecule in the NHS groups. This is achieved by using acidic solutions such as dilute acid solutions to dissolve the crosslinker. If necessary, solubility could also be enhanced by adding biocompatible solvents like ethanol, DMSO, NMP in water based solutions. In another embodiment, glutaric anhydride may be used instead of succinic anhydride to react with lysine. Other anhydrides or acid chlorides that may be used are, e.g., maleic anhydride, succinic anhydride, or fumaryl chloride.

Figure 2:
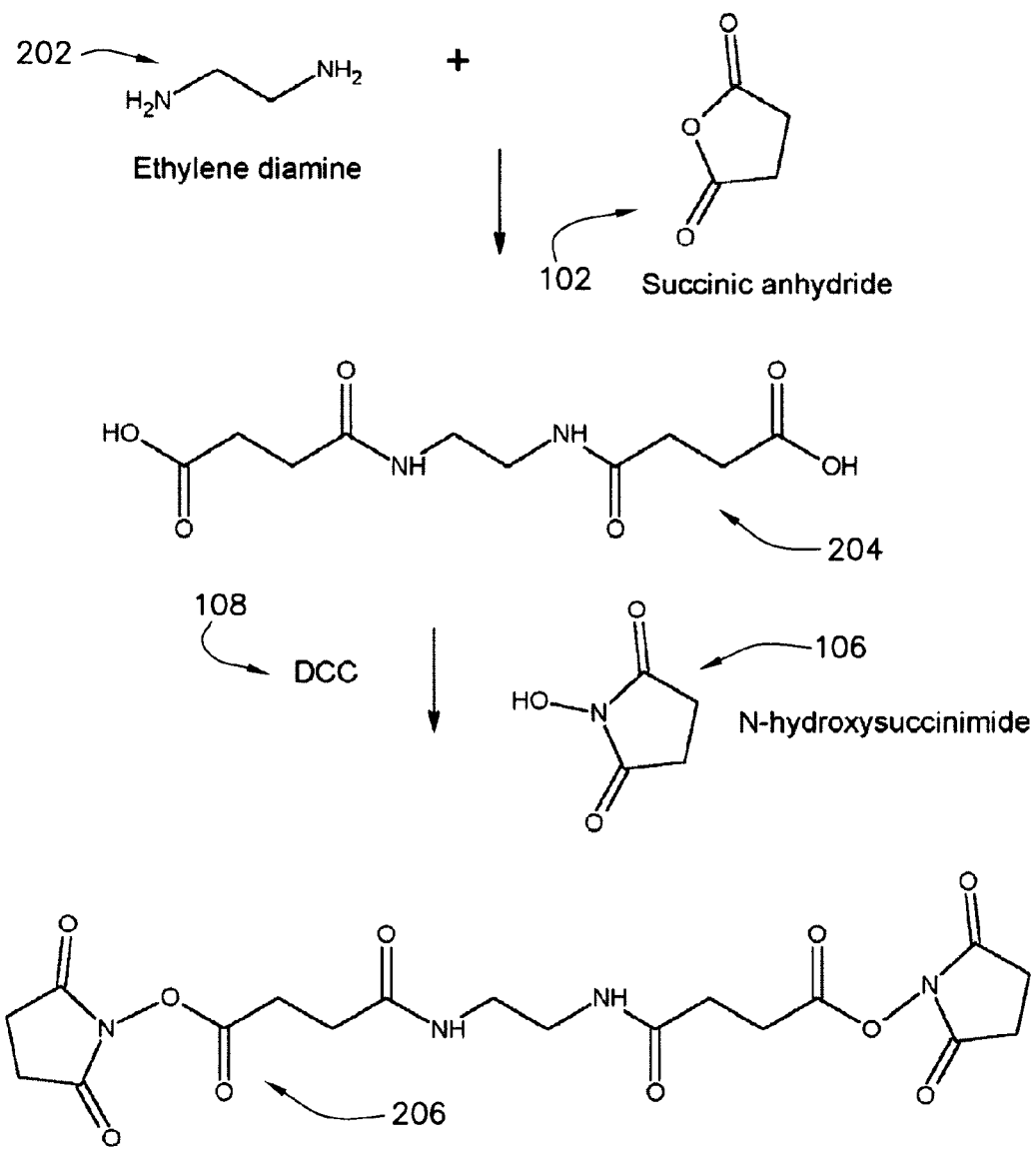
FIG. 2 depicts a synthesis scheme for water soluble crosslinker prepared from ethylene diamine.
Figure 3:
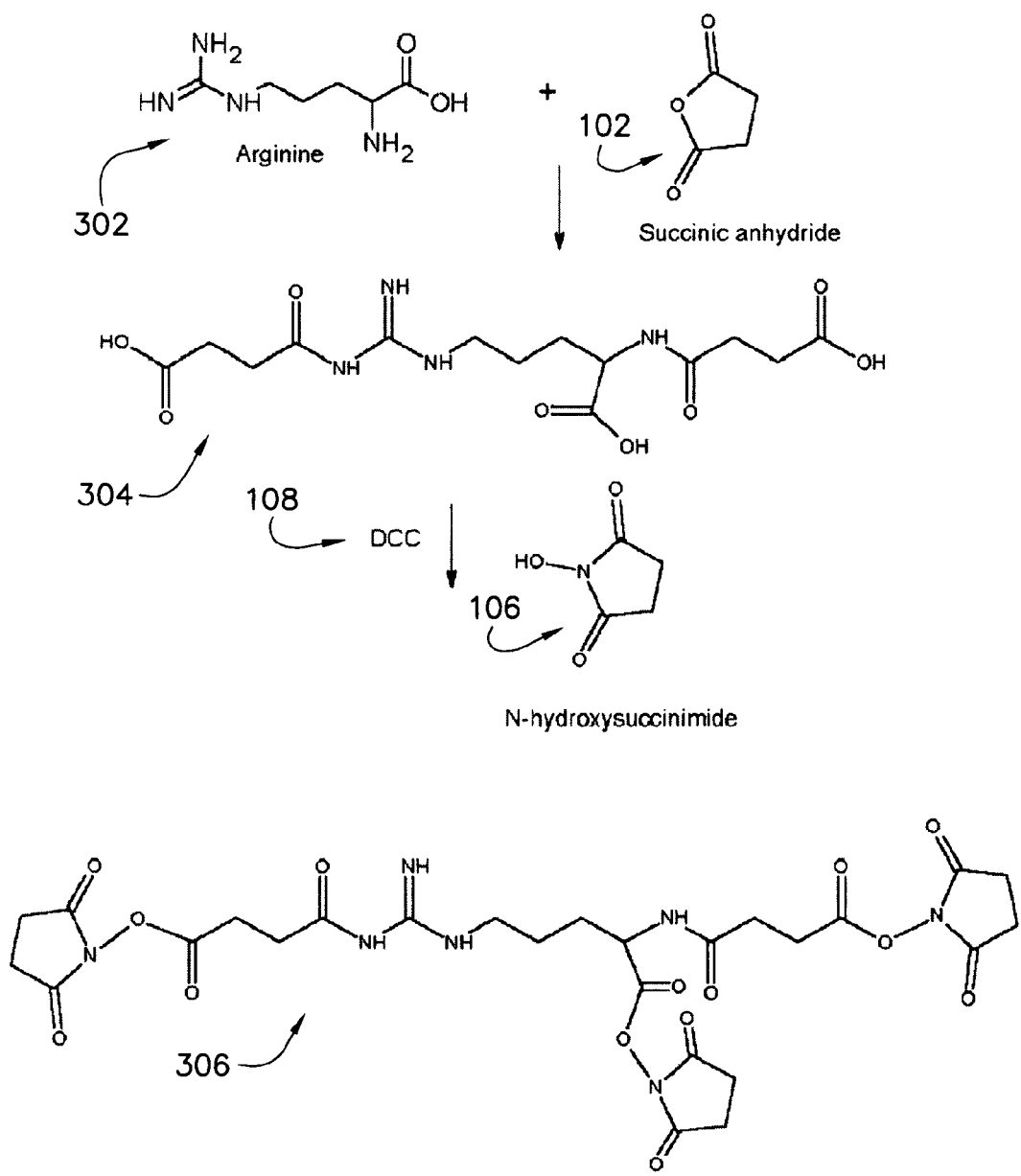
FIG. 3 depicts a synthesis scheme for water soluble aminoacid based crosslinker prepared from arginine.

Other amines may be used. FIG. 2 depicts Scheme II wherein ethylene diamine is used in place of the lysine of Scheme I of FIG. 1. Ethylene diamine 202 is first reacted with excess of succinic anhydride 102 to form an acid terminated amide 204. The acid groups of the acid amide 204 are activated to form 206 by forming n-hydroxysuccinimide ester 106. Figure III depicts Scheme III wherein a diamine such as arginine is used (FIG. 3). Arginine 302 is first reacted with excess of succinic anhydride 102 to form an acid terminated amide derivative 304. The acid groups of acid amide 304 are activated by forming n-hydroxysuccinimide ester 106 with DCC 108 as catalyst. The resultant product 306 has 7 nitrogen atoms with 4-NH functional groups to improve solubility in water.

Figure 4:
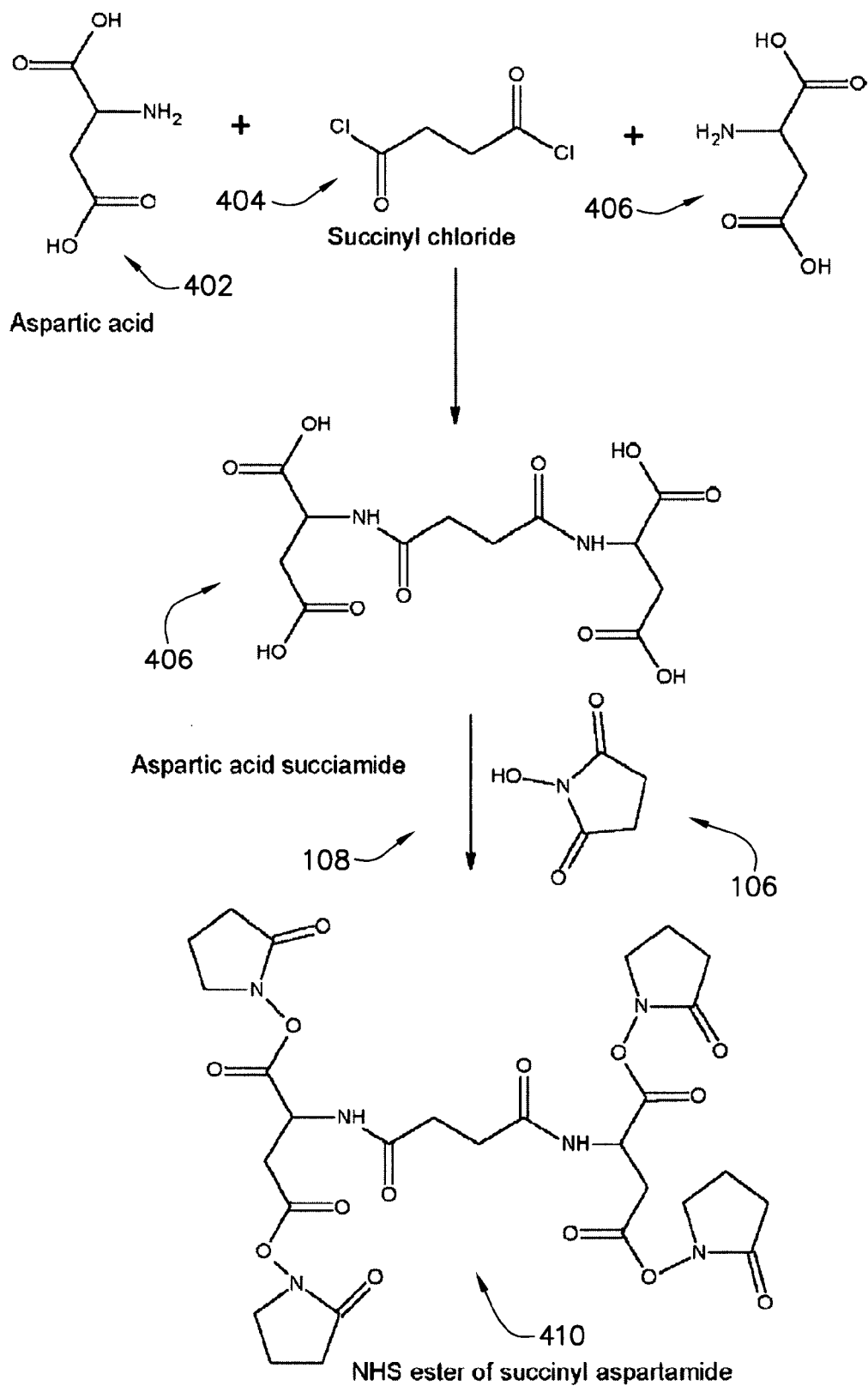
FIG. 4 depicts a synthesis scheme for water soluble aminoacid based crosslinker prepared from aspartic acid.

Other functional groups besides amines may be reacted, e.g., thiols or carboxyls. For instance, FIG. 4 shows Scheme IV using carboxyls wherein an aspartic acid based crosslinker is synthesized. Amine groups of aspartic acid 402 are first reacted with succinyl chloride 404 to produce a tetraacid amide derivative 406. The acid groups of are then reacted with n-hydroxysuccinimide 106 using DCC 108 as a catalyst to produce product 410 having NHS ester (NHS activated acid groups). Using a similar scheme, many other crosslinkers can be synthesized by choosing different combinations of aminoacids, or diacid chloride/anhydrides can be used to form multifunctional aminoacid derivatives. The acid groups of aminoacid derivatives are then activated using n-hydroxysuccinimide groups. Accordingly, many amino acids could be used. These include natural amino acids as well as synthetic amino acids which are not found in the nature. Aspartic acid has 2 acid groups and may be used as a single mer or a polymer, e.g., di, tri, tetramers of aspartic acid, as well as larger polymers. Many diacid chloride/anhydrides may be used in place of succinyl chloride, e.g., glutaryl chloride, glutaric anhydride, maleic anhydride, maleoyl chloride, fumaryl chloride, sebacic anhydride, sebacoyl chloride. Thus, in one embodiment, an aspartic acid is condensed with sebacoyl chloride to produce a tetraacid derivative. The acid groups are then activated using NHS ester.

Biodegradable Crosslinkers and Solvents

The materials described herein may also be made to be biodegradable. Thus crosslinkers, precursors, monomers, or certain of the solvents may be made for biodegradability. In some embodiments, the biodegradability is the result of hydrolysis that spontaneously occurs in aqueous solution, e.g., as in the degradation of an ester or anhydride. Thus some embodiments of the materials degrade in vitro in aqueous solution when exposed to a large excess of water (or buffered water) at room temperature. For instance, about a gram of a hydrolytically degradable crosslinker in the crosslinked or uncrosslinked state placed in about 50 ml of water or phosphate buffered solution (pH 7-7.4) at room temperature can degrade such that it can not be detected be the naked eye. This degradation is in marked contrast to natural materials that require enzymaticly driven degradation. Embodiments include non-polymeric degradable crosslinkers which comprise at least one degradable bond which can be hydrolytically degraded under in vivo conditions.

Other embodiments of the materials include links degradable by enzymatic action, e.g., a peptide sequence degraded by a proteases, e.g., a metalloproteinase. Thus R of Formula I or Formula II may have biodegradable links or bonds that can undergo hydrolysis or biodegradation under physiological conditions (PBS, pH 7.2). In some compositions there may be biodegradable links between an amide group and an activated amide group. Or, for instance, a biodegradable link may be placed between a terminal functional group and an amide group. The degradation of gels containing synthetic peptide sequences degraded by particular proteases will depend on the specific enzyme and its concentration. In some cases, a specific enzyme may be added during the crosslinking reaction to accelerate the degradation process. Poly(lactide) or polyglycolate are examples of degradable materials that may be incorporated. Polylacticacid or poly(lactic acid) or poly(lactide) or PLA is a term used for a polymer which is made from lactide or lactic acid. Similarly PGA is a term used for polyglycolic acid or polyglycolate. Such polymers generally referred as polylactones or polyhydroxyacids.

Figure 5:
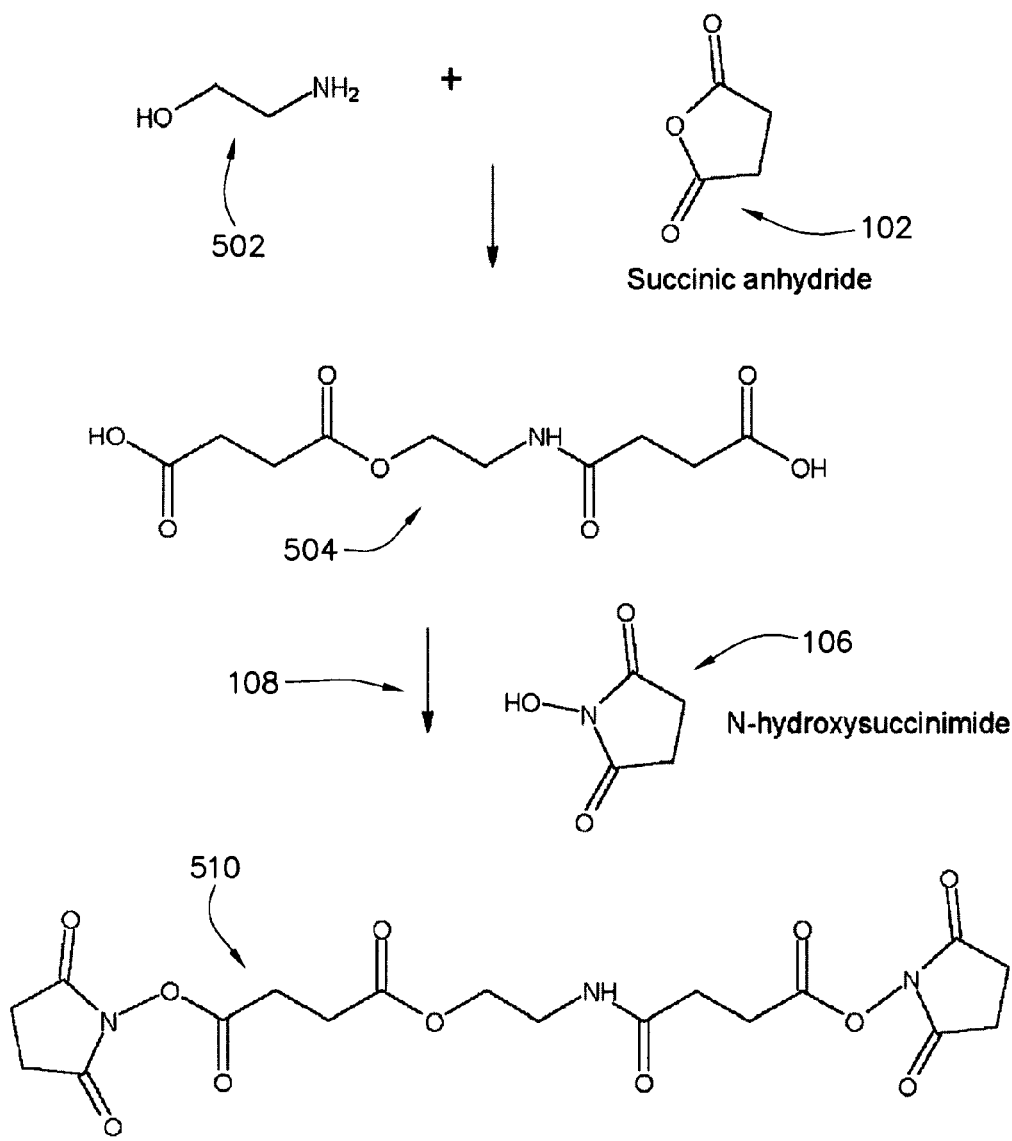
FIG. 5 depicts a synthesis scheme for water soluble biodegradable crosslinker prepared from hydroxy amines.

For instance, FIG. 5 shows Scheme V wherein hydroxyl amine 502 is reacted with succinic anhydride 102 to form 504 having an amido-ester with terminal carboxylic acid group.

The terminal acid groups are then activated using n-hydroxysuccinimide 106. This is achieved by reacting the acid groups with n-hydroxysuccinimide using DCC 108 as a catalyst. The succinate ester in the crosslinker forms product 510 having a hydrolizable bond. The hydrolysis of this ester bond can be controlled by changing a local chemical environment around the ester bond so that the half-life of the bond in aqueous solution may be changed. For example, in one embodiment, a glutaric anhydride is used in place of succinic anhydride. The glutarate ester hydrolyze at a slower rate as compared to succinate ester, apparently due to higher alkyl chain of glutarate ester. Many more hydrolizable crosslinkers can be synthesized by choosing different amine alcohols, and acid chlorides/anhydrides combinations. Examples of amino alcohols include but not limited to are: hydroxy amine, ethanol amine, propanol amine, butanol amine, or hexanol amine. Examples of the acid anhydride/chloride are: glutaryl chloride, glutaric anhydride, maleic anhydride, maleoyl chloride, fumaryl chloride, sebacic anhydride, or sebacoyl chloride. The terminal acid groups may be activated using many different reactive groups. Examples of such groups are: n-hydroxysuccinimide or n-hydroxysulfosuccinimide.

Thus crosslinkers, precursors, monomers, or certain of the solvents may be biodegradable or may have biodegradable bonds. Some of these may have strong electrophilic groups. Such molecules have a wide range of utility, e.g., reagents for the manufacture of crosslinking agents for organic biological systems, crosslinking of tissue, sterilization of bioprosthetic tissue based devices, markers, chemical and biological assay reagents, biotinylation reagents, oil well drilling agents, solubilizing agents, sewage processing, leather processing, or stabilizing agents.

Water Soluble Reactive Monomers

Also disclosed herein are water soluble, nucleophile-reactive monomers which are useful in many fields, e.g., as coatings, or for surface modification or cell encapsulation. Many conventional monomers which can react with water are insoluble in water, e.g., glycidyl methacrylate. This limitation significantly limits the uses of such monomers. Accordingly, novel water soluble reactive monomers disclosed. These include monomers that are reactive with amine functional groups to form covalent bonds. Thus some embodiments are water-soluble monomers (e.g., at least one gram per liter of water solubility) that comprise an unsaturated bond, a strongly nucleophilic functional group, and an ester that is hydrolytically degradable in aqueous solution. The nucleophilic group may be, e.g., a succinimide or succinimidyl ester.

The monomers may be prepared by, e.g., reaction of n-hydroxysulfosuccinimide with an unsaturated acid such acrylic acid or methacrylic acid using g N,N-dicyclohexylcarbodiimide as catalyst. The resultant ester is soluble in water, undergoes free radical polymerization and is reactive toward amine groups, including at a pH of more than about 7. Examples of unsaturated acids which can be reacted with n-hydroxysulfosuccinimide are: acrylic acid, methacrylic acid, itaconic acid, or maleic acid. The sodium, potassium, lithium or other monovalent, divalent or trivalent salts of n-hydroxysulfosuccinimide may be used in reaction with unsaturated acid. The sodium salt of n-hydroxysulfosuccinimide may be used. The sulfonic acid or its salt on a succinimide ring does not affect its reactivity towards amine groups. These monomers could be used, e.g., to introduce polymerizable groups in water soluble macromolecules such as albumin, collagen or similar proteins. Then such macromers could be polymerized.

In one embodiment, components of biological fluid such as proteins (e.g., albumin, fibrinogen, or immune proteins) or polysaccharides are modified to introduce the monomers or other unsaturated polymerizable groups on the biomolecule components. The unsaturated groups in the modified biological fluid are then crosslinked in situ by a free radical polymerization, preferably by photopolymerization reaction. For example, 1 ml of fetal bovine serum may be treated with 20 mg of n-hydroxysuccinimide ester of acrylic acid (ANHS). The ANHS reacts with free amine groups on the proteins such as lysine residues on albumin to form an amide bond with unsaturated end group. The unsaturated modified serum is then mixed with photopolymerization initiator such as IRGACURE 2959™ or eosin-triethanol amine and photopolymerized with long UV light (IRGACURE 2959™) or visible light (514 nm, eosin/triethanol amine).

The conversion of biological fluids to a crosslinked gel composition may be achieved by a chemical reaction with a crosslinker. The specifics of the reaction will depend on the reactive functional groups present in the biological fluid and on the crosslinker, number of reactive groups present on the reactants, concentration of each ingredient, pH, temperature and pressures used. The reaction conditions for crosslinking will depend on the nature of the functional groups. Some reactions are conducted in buffered aqueous solutions at pH 5 to 12. Examples of buffers are sodium borate buffer (pH 10) and triethanol amine buffer (pH 7). In some embodiments, organic solvents such as ethanol or isopropanol may be added to improve the reaction speed or to adjust the viscosity of a given formulation. A non reacting organic solvent such as n-methyl pyrrolidinone also offers stability.

When the crosslinker and functional polymers are synthetic (for example, when they are based on polyalkylene oxide), then it is helpful in some embodiments to use molar equivalent quantities of the reactants. In some cases, molar excess crosslinker may be added to compensate for side reactions such as reactions due to hydrolysis of the functional group.

When choosing the crosslinker and crosslinkable polymer in a biological fluid for reaction by electrophilic-nucleophilic reactions, both the polymers must have more than 2 functional groups per molecule. For example, a difunctional crosslinker cannot form a crosslinked network with another difunctional component. The sum of groups on crosslinker and biological fluid must be greater than five for crosslinking to occur. Thus, a use of monofunctional crosslinker will not form gelation. In most cases, primary amine side groups on proteins such as lysine residues will serve as crosslinking sites. Generally, it is preferred that each biocompatible crosslinked polymer precursor has more than 2 and more preferably 4 functional groups. In the case of unsaturated functional groups, however, a crosslinker may indeed have only two unsaturated groups since each group may contribute to the growth of separate chains.

Examples of reactive functional groups on crosslinkers groups are n-hydroxysuccinimide (NHS) or n-hydroxysulfosuccinimide. Examples of functional groups on biological fluids are primary amines. An advantage of the NHS-amine reaction is that the reaction kinetics leads to quick gelation usually within 10 minutes, more usually within 1 minute and most usually within 10 seconds. This fast gelation is preferred for in situ reactions on live tissue. The NHS-amine crosslinking reaction leads to formation of N-hydroxysuccinimide as a side product. The sulfonated or ethoxylated forms of N-hydroxysuccinimide are preferred due to their increased solubility in water and hence their rapid clearance from the body. The sulfonic acid salt on the succinimide ring does not alter the reactivity of NHS group with the primary amines.

The NHS-amine crosslinking reaction may be carried out in aqueous solutions and in the presence of buffers. Examples are phosphate buffer (pH 5.0-7.5), triethanolamine buffer (pH 7.5-9.0) and borate buffer (pH 9.0-12) and sodium bicarbonate buffer (pH 9.0-10.0). Aqueous solutions of NHS based crosslinkers and functional polymers should preferably be made just before the crosslinking reaction due to reaction of NHS groups with water. Longer "pot life" can be obtained by keeping these solutions at lower pH (pH 4-5).

The crosslinking density of the resultant biocompatible crosslinked polymer is controlled by the overall molecular weight of the crosslinker and functional polymer and the number of functional groups available per molecule. A lower molecular weight between crosslinks such as 600 Daltons will give much higher crosslinking density as compared to a higher molecular weight such as 10,000 Daltons. Higher molecular weight functional polymers are preferred, preferably more than 3000 Daltons, so as to obtain elastic gels. The crosslinking density can also be controlled by the overall percent solids of the crosslinker and functional polymer solutions. Increasing the percent solids increases the probability that an amine group will combine with a NHS group prior to inactivation by hydrolysis. Yet another method to control crosslink density is by adjusting the stoichiometry of amine to NHS groups. A one to one ratio leads to the highest crosslink density.

As described above, a biological fluid (e.g., blood, serum, or fibrinogen rich fractions) may be used for reaction with crosslinkers or the monomers to form a crosslinked gel material. The material may be made in preparation for a medical procedure, e.g., immediately before or during the same, and used with a crosslinker or the monomer. By way of example, biological fluids such as sterile human blood serum or plasma may be mixed with the succinimide ester of poly(vinyl pyrrolidinone-co-acrylic acid) copolymer solution (pH 7.2). The crosslinking reaction is accelerated by raising the pH of the solution. This can be achieved by contacting such composition with suitable alkaline buffer. Nonlimiting examples of suitable alkaline buffers include HEPES, sodium hydroxide, potassium hydroxide, calcium hydroxide, bicarbonate/NaOH pH 10, sodium borate pH 10, 1.5 M glycine/NaOH pH 10, 0.5-0.75M sodium carbonate/bicarbonate pH 10, 1M hydroxyethylepiperazine propane sulfonic acid (EPPS) pH 8.5, Trishydroxymethyl aminoethane sulphonic acid pH 8 and triethanol amine pH 7. The amount of alkaline buffer that is utilized should be enough to induce crosslinking. In some cases, the crosslinker is mixed with the alkaline buffer to raise the pH and then mixed with biological fluid to induce crosslinking or gelation. This method is least preferred due to hydrolysis of n-hydroxysuccimide esters at higher pH. The amine-succinimide ester reaction parameters such as number of reactive functional groups present on the biological fluid components, concentration of each ingredient, pH, temperature and pressures are adjusted such that gelation occurs within 60 minutes, more preferably with in 60 seconds and most preferably with 1 to 10 seconds. Exemplary compositions for gelation and reaction conditions are given in Table 1.

TABLE 1

Crosslinked Gels Formed Using Biological Fluid/Protein and Synthetic Crosslinker Reaction*

| Item | Biological fluid | Crosslinker | Gel time (minutes) | Notes |
|---|---|---|---|---|
| 1 | 30% albumin in PBS | PVPPAANHS, 10% in PBS | 10 seconds | Soft gel |
| 2 | 20% albumin in PBS | PVPPAANHS, 10% in PBS | 2 | Soft gel |
| 3 | 10% albumin in PBS | PVPPAANHS, 10% in PBS | 8 | Soft gel |
| 4 | 5% albumin in PBS | PVPPAANHS, 10% in PBS | 15 | Loose gel |
| 5 | 30% albumin in PBS | BTANHS, 10% in PBS | 1 | Soft gel |

TABLE 1-continued

Crosslinked Gels Formed Using Biological Fluid/Protein and Synthetic Crosslinker Reaction*

| Item | Biological fluid | Crosslinker | Gel time (minutes) | Notes |
|---|---|---|---|---|
| 6 | 20% albumin in PBS | BTANHS, 10% in PBS | 3 | Soft gel |
| 7 | 10% albumin in PBS | BTANHS, 10% in PBS | 18 | Soft gel |
| 8 | 5% albumin in PBS | BTANHS, 10% in PBS | >28 | Did not gel |
| 9 | 30% albumin in PBS | PEGNHS as neat liquid | 30 seconds | Soft gel |
| 10 | 30% albumin in PBS | PEGNHS 10% in distilled water | 2 | Soft gel |
| 11 | 20% albumin in PBS | PEGNHS 10% in distilled water | 8 | Soft gel |
| 12 | 10% albumin in PBS | PEGNHS 10% in D WATER | 23 | Loose gel |
| 13 | 5% albumin in PBS | PEGNHS 10% in distilled water | 35 | Did not gel |
| 14 | 20% albumin in PBS | BTANHS(10%) in PEGNHS | 5 seconds | Soft gel |
| 15 | 5% albumin in PBS | BTANHS(10%) in PEGNHS | 5 | Loose gel |
| 16 | 20% albumin in PBS | BTANHS(10%) in PEG 600 | 5 | Soft gel |
| 17 | 5% albumin in PBS | BTANHS(10%) in PEG 600 | >25 | Did not gel |
| 18 | Human serum | PVPPAANHS, 10% in PBS | 5 | Soft gel |
| 19 | Human blood | PVPPAANHS, 10% in PBS | 7 | Loose gel |

*pH was raised using 3M NaOH solution, at ambient temperature (27° C.) and mixed equal volumes. BTANHS, see Example 2; PEGNHS, see Example 3; PVPPAANHS, see Example 4. PEG 600 is polyethylene glycol with a molecular weight of 600.

pH was raised using 3M NaOH solution, at ambient temperature (27° C.) and mixed equal volumes. BTANHS, see Example 2; PEGNHS, see Example 3; PVPPAANHS, see Example 4. PEG 600 is polyethylene glycol with a molecular weight of 600.

Many low molecular weight crosslinkers such n-hydroxysuccinimide esters of di or polyfunctional acids are generally insoluble in water. For example, n-hydroxysuccinimide esters of C4 to C18 diacids such as glutaric, suberic, sebacic, 1,2,3,4-butanetetracarboxylic acids have very low solubility in water. These can be dispersed in aqueous solution to form a dispersion which can be then mixed with biological fluid for crosslinking and gel formation as already described. A biocompatible surfactant such as polyethylene oxide-polypropylene oxide block copolymer, PLURONIC F127 may be used to emulsify the crosslinker prior to use. The nonlimiting examples of surfactants include: POLYSORBATE 40, POLYSORBATE 80, Tween 40, PLURONICS and TETRONICS. The emulsified crosslinker solution is easy to dispense uniformly during the crosslinking reaction. Alternatively, a biocompatible organic solvent may also be used to dissolve the crosslinker. Nonlimiting examples of organic solvents include; C1-C3 alcohols such as ethanol, 1,2-propylene glycol, glycerol and isopropanol, 1,4-butane diol, 1,6 hexane diol, n-methyl pyrrolidinone, dimethyl sulfoxide, ethyl lactate, acetone, methyl ethyl ketone, polyethylene glycol and its derivatives. Water soluble organic solvents are preferred and n-methyl pyrrolidinone, ethanol, glycerol, propylene glycol and polyethylene glycol 400, methoxy terminated polyethylene glycol are particularly preferred due to their proven safety in human use. Alternatively, liquid crosslinkers disclosed in these inventions may also be used to dissolve the low molecular weight crosslinkers.

Sometimes mixtures of crosslinkers may be used to achieve desirable crosslinking density of the resultant gel. This may be done to achieve quick gelation or to achieve suitable degradation profile of the crosslinked gel. In one embodiment, a mixture of high molecular weight crosslinker (PVPPANHS) and low molecular weight surfactant (BTANHS) was used to crosslink the albumin. In another embodiment, a mixture of PEGNHS and BTANHS was used.

Several biocompatible crosslinked polymers can be produced using the crosslinkers and biological fluids. The crosslinked gel compositions may be produced in variety of shapes and sizes such as films, ropes, rods, plugs, thin or thick sheets, moldings and laminates. These crosslinked may be produced in situ on a tissue or organ or may be produced in the manufacturing plants using methods known in the art or yet to be developed.

Certain combinations of such polymers that might be used to produce such biocompatible crosslinked polymers are described in Table 2, wherein, in the latter, the crosslinker functional groups are N-hydroxy succinimide esters and the functional polymer functional groups are primary amines.

TABLE 2

Exemplary compositions for making crosslinked gels

| Item No. | Biological Fluid or Synthetic Reactant | Crosslinker with or without degradable groups | Preferred Conditions (Molar equivalent of amine and NHS groups preferred) | Notes |
|---|---|---|---|---|
| 1 | Human blood plasma, | PVPPANHS, BTANHS, PEGNHS or mixtures thereof | >10% crosslinker, borate or triethanol amine buffer, pH 7-9 | Useful as thrombin free semi synthetic fibrin glue |
| 2 | Human blood plasma (with anticoagulant) | PVPPANHS, BTANHS, PEGNHS or mixtures thereof | >10% crosslinker, borate or triethanol amine buffer, pH 7-9 >10 mM calcium chloride | Useful as a liquid hemostat |
| 3 | Human serum | PVPPANHS, BTANHS, PEGNHS or mixtures thereof | >10% crosslinker, borate or sodium bicarbonate buffer, pH 7-9 | Useful in wound healing |
| 4 | Human blood | PVPPANHS, BTANHS, PEGNHS | >10% crosslinker, borate or triethanol amine buffer, pH 7-9 | Useful in wound healing |
| 5 | Human blood plasma Supplemented with proteins or synthetic polymers containing amine groups. | PVPPANHS, BTANHS, PEGNHS or mixtures thereof | >10% crosslinker, borate or triethanol amine buffer, pH 7-9 | Faster gelling compositions with improved mechanical properties of the gels. Forms interpenetrating networks. |
| 6 | >15% albumin solution | PVPPANHS, BTANHS, PEGNHS, SulfoNHS or NHS esters of diacids suberic acid, glutaric acid, sebacic acid or mixtures thereof | >10% crosslinker, borate or sodium bicarbonate buffer, pH 7-9 | Replaces cytotoxic glutaraldehyde from commercially available albumin glue. |
| 7 | >15% albumin solution | BTANHS or similar water insoluble crosslinker | >10% crosslinker, borate or sodium bicarbonate buffer, pH 7-9, 1% PLURONIC F127 as surfactant | Uses surfactants to emulsify crosslinker |
| 8 | >15% solution of amine terminated polyethylene glycol, 4 amines per molecules in alkaline buffer | PVPPANHS or BTANHS in PBS | >10% crosslinker, borate or sodium bicarbonate buffer, pH 7-9, molar equivalent | Synthetic Poly(vinyl pyrrolidinone) and Polyethylene glycol crosslinked compositions. |
| 9 | Albumin, fibrinogen or amine containing synthetic polymer | Liquid crosslinkers such as PEGNHS | >10% crosslinker, borate or sodium bicarbonate buffer, pH 7-9, molar equivalent | Fast gelling compositions |
| 10 | >10% fibrinogen solution | PVPPANHS, BTANHS, PEGNHS or mixtures thereof | >10% crosslinker, borate or sodium bicarbonate buffer, pH 7-9, molar equivalent | Replaces calcium and thrombin from commercial fibrin glue formulations |
| 11 | Fibrinogen rich and thrombin mixture. Calcium depleted to prevent thrombin-fibrinogen reaction | PVPPANHS, BTANHS, PEGNHS or mixtures thereof | >10% crosslinker, borate or triethanol amine buffer, pH 7-9 >10 mM calcium chloride | Crosslinks proteins using enzymatic reaction and synthetic crosslinking reaction. Calcium in crosslinker solution triggers fibrin clotting cascade with thrombin and clotting factors present in fibrinogen solution |

Applications

The crosslinkers are generally useful to form crosslinked materials, e.g., surgical adhesives, glues, dressings, hemostatic agents, wound healing agents, depots for drug delivery, or sealants by using the crosslinkers to react with natural or synthetic precursors. For example, crosslinkers can be reacted with human or bovine albumin solution (e.g., about 10 to about 50% solution in water or aqueous buffer) or synthetic polymers with reactive functional groups (with or without biodegradable groups) to form a crosslinked material. Monomers may also be used in a polymerization reaction to form crosslinked materials. Solvents may be combined with the crosslinkers, monomers, or macromers. Compositions that have no solvents, or are free of water, may also be formulated to make materials in situ. Where convenient, a crosslinked gel material may include a visualization agent (e.g., where a sealant is used in a laproscopic method).

Crosslinked gels may be used in a variety of clinical applications, e.g., as in Schlag & Redl, Fibrin Sealant in Operative Surgery (1986) Vol. 1-7, and include, for example, cardiovascular surgery, orthopaedic surgery, neurosurgery, ophthalmic surgery, general surgery and traumatology, plastic reconstruction and maxillofacial surgery, otorhinolaryngology, and the like.

Some embodiments are directed to in situ formation of a material, which refers to forming a material at its intended site of use. Thus a hydrogel may be formed in situ in a patient at the site wherein the hydrogel is intended to be used, e.g., as a sealant, wound dressing, or drug depot for controlled release. If the material is a gel used as a surgical sealant, the crosslinked gel can be utilized in humans or in other mammals, e.g., dogs, cats, cows, pigs, or buffaloes. Medical applications for a sealant include, e.g., connecting tissue or organs, stopping bleeding, healing wounds, sealing a surgical wound. Or the crosslinked materials may be used for tissue engineering applications such as providing matrix for cell growth or coating of vascular grafts. The dosage of the crosslinking composition will depend upon its intended use. In most surgical application applications 1 to 500 ml total volume of biological fluid (or other precursor fluid) and crosslinker introduced in situ will be sufficient but other volumes may be used as needed; artisans will immediately appreciate that all the ranges and values within the explicitly stated ranges are contemplated.

Some embodiments are fibrin glues that use a crosslinker instead of thrombin and/or factor XIII and/or calcium. Fibrin glues have a first fibrinogen-containing component that is combined with a second component that has thrombin and/or factor XIII for crosslinking the fibrinogen, usually in the presence of excess calcium ions. The fibrinogen portion of fibrin glues have been applied to a tissue repair site either simultaneously or sequentially with a thrombin/calcium ion setting composition. Accordingly, the fibrinogen portion of a fibrin glue, or other fibrinogen-enriched composition, may be applied with a crosslinker or monomer to make a crosslinked fibrin material. In some embodiments, the fibrinogen component, the crosslinker components, or the entire system is essentially free of water so as to enhance storage, delivery, or reaction; biocompatible solvents may be used as need to solubilized the components.

Some embodiments are directed to minimally invasive surgery (MIS). MIS refers to surgical techniques such as laparoscopy, thoracoscopy, arthroscopy, intraluminal endoscopy, endovascular techniques; catheter based cardiac techniques (such as balloon angioplasty) and interventional radiology.

Biological fluids, natural precursors, or synthetic precursors and the crosslinker components may simply be applied sequentially or simultaneously to the tissue repair site via a needle or syringe or other application system to form crosslinked materials from the precursors. In certain embodiments, it is preferred to apply the components sequentially so as to prime the tissue. Where the tissue is primed, a first component, e.g., the crosslinker, is applied to the tissue repair site. Next, the other precursor, e.g., in a biological fluid, is applied.

Accordingly, devices used for delivery of fibrin glues may be modified for delivery of precursors (e.g., crosslinkers, monomers, or biological fluids) as appropriate for a specific application. Instead of manually applying a biological fluid-crosslinker to a tissue repair site, one may use specialized devices for applying the two components system such as developed for the application of fibrin glue. These and other representative devices which may be adapted for such uses include those described in U.S. Pat. Nos. 6,165,201, 6,152,943, 4,874,368; U.S. Pat. No. 4,631,055; U.S. Pat. No. 4,735,616; U.S. Pat. No. 4,359,049; U.S. Pat. No. 4,978,336; U.S. Pat. No. 5,116,315; U.S. Pat. No. 4,902,281; U.S. Pat. No. 4,932,942; PCT Application WO 91/09641, and Tange, R. A., Fibrin Sealant in Operative Medicine: Otolaryngology-Vol. 1 (1986), the disclosures of which are herein incorporated by reference herein.

The subject crosslinked compositions according to the subject invention may also be used for biologically bioactive agent delivery e.g., drug delivery. Bioactive agents of interest which may be delivered with the compositions as described above include, e.g., proteins, carbohydrates, nucleic acids, and inorganic and organic biologically active molecules, where specific bioactive agents include, e.g., enzymes, antibiotics, antineoplastic agents, local anesthetics, hormones, antiangiogenic agents, antibodies, neurotransmitters, psychoactive drugs, growth factors, drugs affecting reproductive organs, and oligonucleotides, e.g., antisense oligonucleotides. Various therapeutic agents that may be included are also set forth in U.S. Pat. No. 6,566,406 or U.S. Pat. No. 6,632,457. To prepare a crosslinked gel for a drug delivery application, one may simply combine the active agent with one or both precursors and crosslink them to form a gel. Administration may be by any convenient means, such as syringe, cannula, trochar, and the like. Such methods of drug delivery find use in both systemic and local administration of an active agent.

In one embodiment, the active agent or agents are present in a separate phase from the crosslinked gel. The separate phase protects the crosslinked gel while it is being formed from adverse effects of the active agent and/or modulates the release kinetics of the active agent from the gel, where "separate phase" could be: oil (oil-in-water emulsion); biodegradable vehicle; and the like. For instance, U.S. Pat. No. 6,632,457 which is hereby incorporated by reference herein for all purposes to the extent it does not contradict what is explicitly disclosed herein discloses motifs that may be adapted for use herein. Biodegradable vehicles in which the active agent may be present include: encapsulation vehicles, such as microparticles, microspheres, microbeads, micropellets and the like, where the active agent is encapsulated in a bioerodible or biodegradable polymer such as: polyanhydride, polyglycolic acid, polylactic acid, polyorthocarbonate, polycaprolactone, polytrimethylene carbonate or their copolymers; caging or entrapping molecules, such as cyclodextrins and the like, etc. Biodegradable vehicle protected active agents are preferred where the active agent is an antibiotic, e.g., gentamycin, tetracylcine. A crosslinked gel may be formed in situ to serve as a drug delivery depot.

While various illustrative uses of the compositions have been described above, as explained above the subject methods are not limited to the preparation of crosslinked gel made out of biological fluids, but can be used to produce other gels as well. For example, by selecting the appropriate amine group containing polymer such as amine terminated polyethylene oxide, polylysine, fibrinogen, fibrinogen monomer or albumin solutions, one can prepare various types of crosslinked compositions. The crosslinked compositions made using human blood, blood plasma and blood serum are advantageous in some applications because human blood contains variety of biologically active components known or yet to be discovered such as various growth factors (platelet growth factor), enzymes (tPA, thrombin) and the like. This method of crosslinking permits to trap such biologically active components in a crosslinked polymeric matrix and released them in a controlled manner. The subject methods and compositions may also be used in immobilization of cells, bacteria, virus and the like biological materials. In one embodiment, human blood is used to form a crosslinked gel in which red blood cells and platelets were encapsulated.

The subject invention also provides kits, e.g., clotting or sealant kits. A kit may have as a first component a crosslinker capable of crosslinking biological fluids such as human blood or its derivatives. The first component can optionally contain an alkaline buffer and may also provide a source of calcium ions. The second component may be an alkaline buffer that can optionally contain thrombin, fibrinogen, fibrinogen monomer, amino terminated polyethylene glycol or albumin. Optionally, the kit may also contain liquids such as sterile saline solution which can be added to the first or second components and instructions for preparing such dilutions.

In some embodiments, precursors with functional groups are stored in essentially dry conditions free of water. Since n-hydroxysuccinimide esters, for instance, are reactive with moisture, such esters and their reactants can be packaged under inert gas atmosphere. The inert atmosphere may be nitrogen atmosphere or carbon dioxide atmosphere. Such packaging is likely to improve storage time. It may also permit ambient temperature storage of such compositions.

In some embodiments, a precursor or solvent is melted prior to use. The melting can be done outside the body just prior to use or inside the human or animal body and used. Some of crosslinkers such as 4 arm-n-hydroxysuccinimide ester of polyethylene glycol carboxymethylene-butyric acid, average molecular weight 10000 Daltons (Shearwater 4 arm CM-HBA-NS-10K) have low melting point below 70° C. and can be melted 'in situ' in a surgical environment prior to reaction with biological fluids. Any known method to melt the solid may be used these include and but not limited to, electrical heating, photothermal heating, heating inducted by ultrasonic waves, infrared heaters and lasers. Certain additives such as non-toxic fillers or plasticizers may be added to control the viscosity or melting point of the crosslinker.

Some embodiments are directed to use of biological fluids as a composition having precursors that can be crosslinked to form a material. The biological fluid can be introduced in the human body during a surgical procedure. Such biological fluid compositions may be an aqueous composition that comprises one or more proteins of interest, where such compositions include both naturally occurring compositions, such as physiologically derived fluids, e.g. blood, plasma, serum, urine, cerebrospinal fluid, tears, saliva, milk, mucus, peritoneal cavity fluid and the like; and synthetically prepared compositions, e.g. tissue culture medium, tissue culture medium containing recombinant proteins, synthetic polymer containing protein like functional groups such amine terminated polyethylene glycol, amine terminated polyethers, JEFFAMINE™, and the like or mixtures of thereof. Physiological fluids of interest may be obtained from a variety of hosts, including cows, sheep, pigs, deer, humans and the like. For example, the subject methods can be used to produce enriched protein compositions from cow or sheep milk, where the cow or sheep may be a transgenic animal engineered to produce milk containing a recombinant protein of interest. The recombinant protein or protein mixtures of interest include but not limited to albumin, fibrinogen and the like and mixtures thereof.

Applications for Occluding Blood Vessels or Treating Vessel Surfaces and Tissues Some embodiments relate to release of a precursor into a blood vessel to crosslink the blood fluid or other biological fluid in the blood vessel. In general, a crosslinker, monomer, or macromer is released into the blood vessel and allowed to for a gel with the proteins or other biomolecules in the vessel. Strongly electrophilic crosslinkers will spontaneously react with the biomolecules to form the gel. Monomers or macromers with polymerizable unsaturations may be initiated to form the gel, for instance by use of a redox polymerization system, as in U.S. Pat. No. 6,152,943, or by photopolymerization as in U.S. Pat. No. 5,410,016, each of which are hereby incorporated by reference herein to the extent they do not contradict what is explicitly disclosed herein. The various embodiments of the precursors already described may be used, e.g., liquid crosslinkers, small crosslinkers, or crosslinkers with aqueous or organic solvents.

Figure 6:
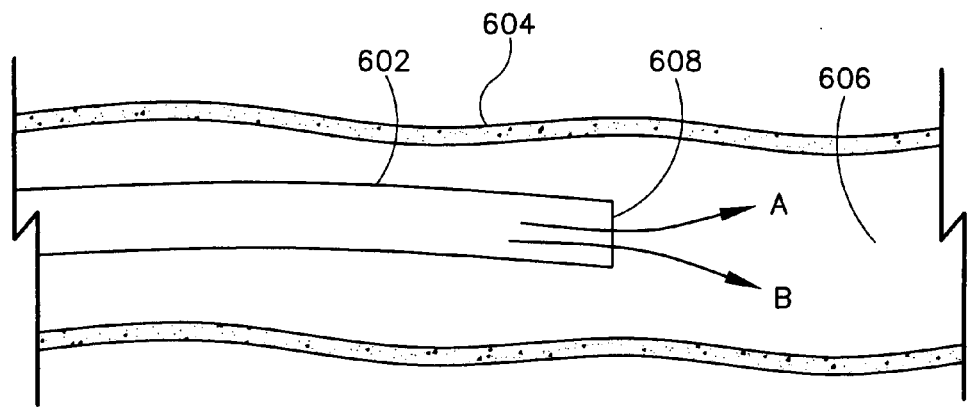
FIG. 6 depicts a precursor being released into a biological fluid in a patient to crosslink biomaterials in the fluid.

Some applications relate to occluding a vessel. As shown in FIG. 6, a catheter 602 is deployed in blood vessel 604 that has whole blood 606 therein. A precursor, e.g., a crosslinker, is pumped down the catheter 602 and released through catheter end 608 into blood vessel 604 as indicated by arrows labeled A or B. The precursor forms a gel material in the vessel (not depicted).

Figure 7A:
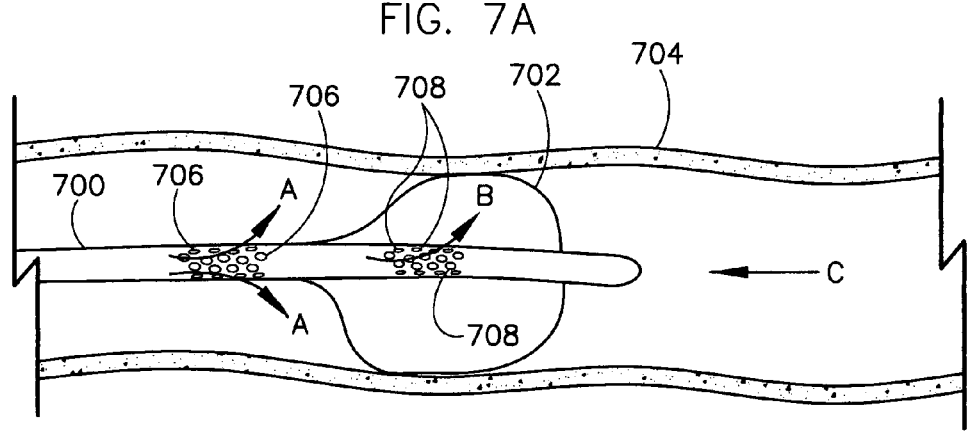
FIG. 7A depicts a reversibly inflatable occlusive device for directing the flow of precursors released into a blood vessel.
Figure 7B:
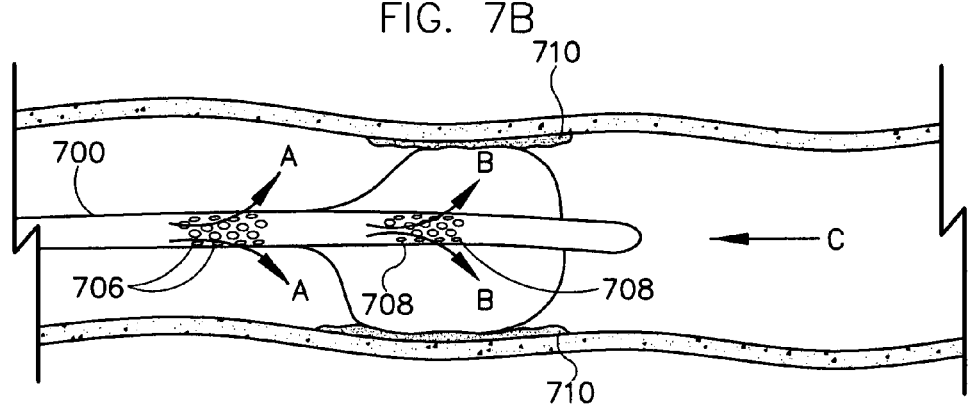
FIG. 7B depicts the device of FIG. 7a as used to form a material on the lumen of the blood vessel.

Some applications relate to forming a material on the walls of a biological vessel. FIG. 7A depicts a catheter 700 equipped with reversibly inflatable occlusive device 702 for directing the flow of precursors as indicted by arrows A showing precursors released through openings 706 into a blood vessel 704. The precursor may be used to inflate the occlusive device 702 as indicated by arrows B, with the precursor flowing into the occlusive device through openings 708. FIG. 7B depicts the device of FIG. 7a being moved as per arrow C while precursors enter the vessel. As the precursors react, the movement of occlusive device 702 forces them against the lumen of the vessel where the formation of crosslinked material 710 is completed, with the blood fluids and the materials on the walls of the vessel being crosslinked together. The rate of the formation of the material can thus be matched to the rate of movement of the occlusive device to control the material's formation. A reaction that is very fast relative to the occlusive device's movement will tend to form the material with loose association with the walls of the vessel. Slower reactions will tend to force the gelling material against the walls of the vessel, with the balloon forcing the materials against the wall and entrapping the precursors, which continue to react with the material to form crosslinks. FIGS. 7A and 7B demonstrate broadly applicable principles for forming a material on a vessel's walls.

Figure 8A:
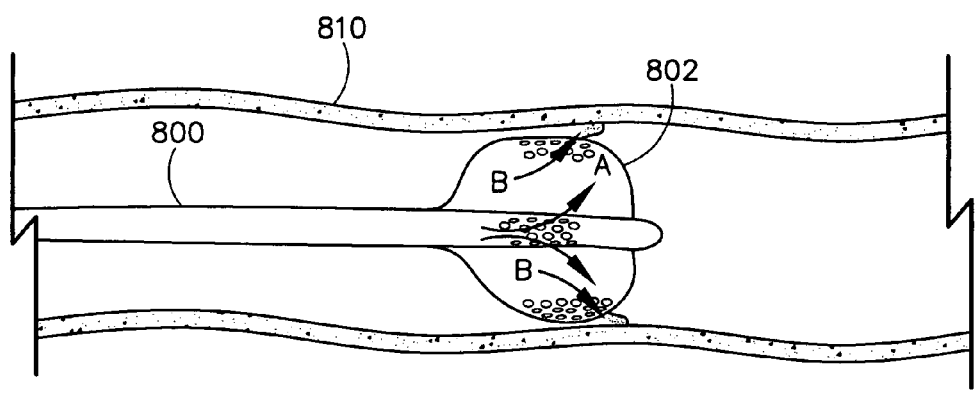
FIG. 8A depicts an alternative device for directing the flow of precursors released into a blood vessel.
Figure 8B:
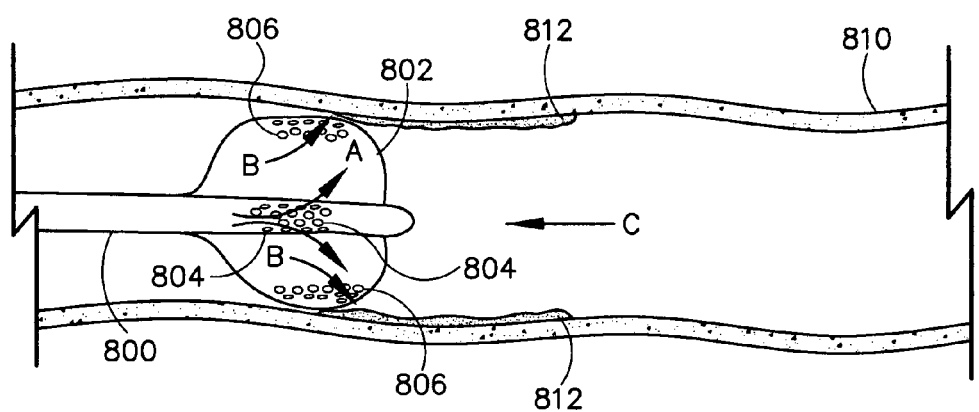
FIG. 8B depicts the device of FIG. 8A as used to form a material on the lumen of the blood vessel.

These principles may be applied, for instance, as in FIGS. 8A and 8B. FIG. 8A depicts catheter 800 equipped with reversibly inflatable occlusive device 802 for directing the flow of precursors. Precursors are pumped through catheter 800 and flow through openings 804 as indicated by arrows A into occlusive member 802 that has openings 806 that allow the precursors to flow into vessel 810 as indicated by arrows B. The precursors crosslink blood in vessel 810 to form material 812 as catheter 800 is moved in the direction indicated by arrow C.

In some embodiments, the expandable device is coated with the crosslinker. A guidewire is placed in the vessel and a catheter is passed over the guidewire. The expandable device mounted on an inflation guidewire is passed through the catheter to the site of interest. It is passed into the vessel and expanded to contact the vessel wall, where the crosslinker reacts with the blood to form the crosslinked material. The coating may be made by placing a liquid crosslinker directly on a suitable occlusive device or using solvents or excipients, e.g., waxes, aliphatics, or release rate modifying agent as in U.S. Pat. No. 6,632,457, which is hereby incorporated by reference herein for all purposes to the extent it does not contradict what is explicitly disclosed herein. In some embodiments, the crosslinker is made into a paste or solid at room temperature and becomes more liquid or less viscous at physiological temperatures to facilitate the release of the crosslinker from the coating or device.

The precursor may be delivered in combination with a drug to be delivered locally. Examples of such drugs are clopidogrel, taxols, rapamycin, or statins. The drug may be mixed with the precursor or coating or delivered through a catheter before, during or after the procedure.

One application of the crosslinked materials is to serve as depots for local drug delivery. As such, they may be placed as needed in the patient, e.g., a blood vessel, tract, cardiac area, or other tissue. In some embodiments, the materials are used to overcoat debrided or traumatized tissues. For instance, balloon angioplasty techniques can disrupt the vessels wherein they are used. Or, for instance, debridement or tissue-removing techniques can usefully reduce unwanted tissue or scars but leave traumatized tissues and can leave irregularly-shaped areas. Formation of the material over these surfaces can have a favorable physiological effect, e.g., as by providing a blood-compatible surface. Moreover, the release of drugs onto such tissues is useful. For instance, anti-inflammatories may be delivered, or other agents, e.g., antibiotics, antimitotics, cytokines, or extracellular matrix molecules.

In some embodiments, the expandable device is a coronary stent, with precursors placed on the stent or forming a coating around the stent. Various devices may be coated as appropriate, e.g., as in some examples of guidewire-based devices are provided in, e.g., U.S. Pat. Nos. 5,540,707; 5,935,139; 6,050,972; 6,371,970; 6,875,193; 6,800,080; which are hereby incorporated by reference herein to the extent they do not contradict what is explicitly disclosed herein. Crosslinkers on the coating form a prophylactic material around the stent that provides for enhanced biocompatibility, each of which are hereby incorporated by reference to the extent they do not contradict what is explicitly disclosed herein.

EXAMPLES

Materials and Equipment

Polyethylene glycols can be purchased form various sources such as Shearwater Polymers, Union Carbide, Fluka and Polysciences. Multifunctional hydroxyl and amine terminated polyethylene glycol are purchased from Shearwater Polymers, Dow Chemicals and Texaco. PLURONIC® and TETRONIC® series polyols can be purchased from BASF Corporation. DL-lactide, glycolide, caprolactone and trimethylene carbonate can be obtained from commercial sources, e.g., Purac, DuPont, Polysciences, Aldrich, Fluka, Medisorb, Wako and Boehringer Ingelheim. N-hydroxysulfosuccinimide can be purchased from Pierce, USA. Other reagents and solvents are of reagent grade and can be purchased from commercial sources such as Polysciences, Fluka, Aldrich and Sigma. The reagents/solvents are typically purified/dried using standard laboratory procedures such as described in Perrin et al. Small laboratory equipment and medical supplies can be purchased from, e.g., Fisher or Cole-Parmer.

General Analysis

Chemical analysis for the polymers synthesized include structural determination using nuclear magnetic resonance (proton and carbon-13), infrared spectroscopy, high pressure liquid chromatography and gel permeation chromatography (for molecular weight determination). Thermal characterization such as melting point and glass transition temperature can be done by differential scanning calorimetric analysis. The aqueous solution properties such as micelle formation, gel formation can be determined by fluorescence spectroscopy, UV-visible spectroscopy and laser light scattering instruments.

In vitro degradation of the polymers is followed gravimetrically at 37° C., in aqueous buffered medium such as phosphate buffered saline (pH 7.2). In vivo biocompatibility and degradation life times may be assessed by injecting or forming a gelling formulation directly into the peritoneal cavity of a rat or rabbit and observing its degradation over a period of 2 days to 12 months. Alternatively, the degradation may be assessed by the prefabricated sterile implant made by processes such as casting the crosslinker-biological fluid composition in molds. The implant is then surgically implanted within the animal body. The degradation of the implant over time is monitored gravimetrically or by chemical analysis. The biocompatibility of the implant can be assessed by standard histological techniques.

Example 1 Synthesis of Polyvinyl Pyrrolidinone Based Crosslinker

Synthesis of N-hydroxysuccinimide (NHS) Ester of poly(vinyl pyrrolidinone-co-acrylic acid) Copolymer (PVPPANHS)

1 g poly(vinyl pyrrolidinone-co-acrylic acid) copolymer (Aldrich, Catalog number 41,852-8) and 0.4 g of N-hydroxysuccinimide were transferred to 100 ml round bottom flask. The mixture was dissolved in 10 ml dry dimethyleformamide (DMF). The solution was then cooled to 0° C. using ice bath. 0.72 g of N,N-dicyclohexylcarbodiimide (DCC) dissolved in 5 ml dry DMF was added to the reaction mixture dropwise. The reaction mixture was kept at 0° C. for 2 h and then at room temperature for 12 to 24 h. The reaction mixture was protected from moisture during the entire work up. At the end of the reaction, the precipitated dicyclohexylurea was removed by filtration. The filtrate was then added to 200-500 ml diethyl ether. The precipitated polymer was recovered by decantation or filtration. The product, a thick viscous liquid, was further purified by washing with 10-20 ml diethyl ether. The IR spectrum showed imide carbonyl at 1780 cm-1 and cyclic C—N at 1380 cm-1. The NHS ester was stored at −20° C. until use.

Example 2 Synthesis of Low Molecular Weight Tetrafunctional Crosslinker (Water Insoluble)

Synthesis of N-hydroxysuccinimide Ester of 1,2,3,4-butanedicarboxylic Acid (BTANHS)

In 100 ml round bottom flask, 1.0 gram 1,2,3,4-butanedicarboxylic acid, 2.0 g N-hydroxysuccinimide and 10 ml tetrahydrofuran (THF) were added and the flask was cooled 0° C. using ice bath. 3.5 g N,N-dicyclohexylcarbodiimide dissolved in 5 ml THF were added while stirring. The reaction mixture was stirred at 0° C. for 2-4 h and then at room temperature overnight. The precipitated dicyclohexylurea was removed by filtration and the solution was concentrated by removing the solvent. The crude light yellow solid product was purified by recrystallization. The IR spectrum showed imide carbonyl at 1780 cm-1 and cyclic C—N at 1380 cm-1.

Example 3 Synthesis of Liquid Crosslinker

Synthesis of poly(ethylene glycol) N-hydroxysuccinimide ester(PEGNHS)

In 100 ml round bottom flask, 2 gram polyethylene glycol 600 diacid (Fluka, catalog 81324), 0.8 g N-hydroxysuccinimide and 10 ml methylene chloride were added and the flask was cooled 0 C using ice bath. 1.4 g N,N-dicyclohexylcarbodiimide dissolved in 5 ml methylene chloride was added while stirring. The reaction mixture was stirred at 0 C for 2-4 h and then at room temperature overnight. The precipitated dicyclohexylurea was removed by filtration and the solution was concentrated by removing the solvent. The crude light yellow liquid product was purified by washing with 10 ml diethyl ether. The IR spectrum showed imide carbonyl at 1780 cm-1 and cyclic C—N at 1380 cm-1.

Example 4 Crosslinking of Proteins Solution Using Water Soluble Poly(vinyl Pyrrolidinone) Based Crosslinker

Crosslinking of 30% Albumin in Phosphate Buffered Saline (PBS) Solution Using PVPPANHS 100 g of PVPPANHS was dissolved in 1 ml PBS. 333 mg bovine serum albumin was dissolved in 0.667 ml PBS. 20 microliter PVPPANHS solution in PBS and 20 microliter albumin solution were mixed on a glass plate to form a uniform solution. Addition of 20 microliter 3M sodium hydroxide to PVPPANHS-albumin mixture transformed the solution into soft hydrogel in 20 seconds. The resultant hydrogel was insoluble in water indicating formation of crosslinked network.

Example 5 Crosslinked PVP-Polyalkylene Oxide Copolymers

Crosslinking of Amine Terminated Polyethylene Glycol Using PVPPANHS 100 g of PVPPANHS is dissolved in 0.9 ml PBS. 300 mg of amine terminated 4 arm polyethylene glycol 4000 (APEG, from Shearwater Polymers, USA) is dissolved in 0.700 ml PBS. 20 microliter of PVPPANHS solution in PBS and 20 microliter of APEG solution are mixed on a glass plate to form a uniform solution. Addition of 20 microliter 3M sodium hydroxide to PVPPANHS-albumin mixture transforms the solution into crosslinked hydrogel.

Example 6 Crosslinking of Protein Mixtures and Enzymes Using Synthetic Water-Soluble Crosslinker

Crosslinking of Human Blood Plasma Using PVPPANHS 100 mg of PVPPANHS was dissolved in 0.9 ml PBS. 20 microliter of PVPPANHS solution in PBS and 20 microliter of human blood plasma were mixed on a glass plate to form a uniform solution. Addition of 20 microliter 3M sodium hydroxide to PVPPANHS-blood plasma mixture transformed the solution into soft hydrogel in 7 minutes. The resultant semisynthetic clot is insoluble in PBS indicating crosslinking of blood plasma. In some cases, human blood plasma may be mixed other polymers such as human serum albumin or amine terminated polyethylene glycol for faster gelation and increasing crosslinking density.

Example 7 Encapsulation of Mammalian Cells and Enzymes Using Polyvinyl Pyrrolidinone Based Crosslinker

Gelation of Human Blood Using PVPPANHS Solution 100 g of PVPPANHS was dissolved in 0.9 ml PBS. 20 microliter of PVPPANHS solution in PBS and 20 microliter of fresh human blood were mixed on a glass plate to form a uniform dispersion. Addition of 20 microliter 3M sodium hydroxide to PVPPANHS-blood dispersion transformed the solution into soft hydrogel in 10 minutes. The dark red colored crosslinked solid was insoluble in PBS. Cells in the blood are trapped inside the gel and are thus encapsulated in the gel.

Example 8 Crosslinking of Proteins Solution Using Water Soluble Poly(vinyl pyrrolidinone) Based Crosslinker

Crosslinking of 20% Bovine Fibrinogen Solution Using PVPPANHS 100 g of PVPPANHS was dissolved in 0.9 ml PBS. 0.200 mg of bovine fibrinogen was dissolved in 0.800 ml PBS. 20 microliter PVPPANHS solution in PBS and 20 microliter of fibrinogen solution were mixed on a glass plate to form a uniform solution. Addition of 20 microliter 3M sodium hydroxide to PVPPANHS-fibrinogen mixture transformed the solution into hydrogel.

Example 9 Crosslinking of Proteins Solution Using Water Insoluble Crosslinker

Crosslinking of 30% Albumin Solution Using BTANHS Dispersion in PBS 100 g of BTANHS was dispersed in 0.9 ml PBS. 333 mg of bovine serum albumin was dissolved in 0.667 ml PBS. 20 microliter BTANHS dispersion in PBS and 20 microliter of albumin solution were mixed on a glass plate to form a uniform dispersion. Addition of 20 microliter 3M sodium hydroxide to BTANHS-albumin mixture transformed the solution into soft hydrogel in 5 minutes. The resultant hydrogel was insoluble in water indicating formation of crosslinked network.

Example 10 Crosslinking of Proteins Solution Using Water Insoluble Crosslinker Emulsion Crosslinking of Albumin Solution Using BTANHS Emulsion in PBS 200 g of BTANHS was dispersed in 0.8 ml PBS containing 2% PLURONIC F127 (from BASF corporation USA) as a surfactant. Sonication or high speed stirring helps to form the emulsion. 333 mg bovine serum albumin was dissolved in 0.667 ml PBS. 20 microliter BTANHS emulsion in PBS and 20 microliter of albumin solution were mixed in a 1 ml plastic centrifuge tube to form a uniform solution. Addition of 20 microliter triethanol amine to albumin-BTANHS mixture transformed the solution into soft hydrogel in 3 minutes.

Example 11 Crosslinking of Proteins Solution Using Crosslinker Dissolved in Biocompatible Organic Solvent Crosslinking of Albumin Solution Using BTANHS Solution in Polyethylene Glycol 600

100 g of PEGNHS was dissolved in 0.8 ml polyethylene glycol 600. Polyethylene glycol serves as an organic solvent. 200 mg bovine serum albumin was dissolved in 0.800 ml PBS. 20 microliter of PEGNHS solution in polyethylene 600 solution and 20 microliter of albumin solution were mixed on a glass plate. Addition of 20 microliter 3M sodium hydroxide solution to Albumin-PEGNHS mixture transformed the solution into soft rubbery hydrogel in 5 minutes.

Example 12

Crosslinking of Proteins Solution Using Liquid Crosslinker 333 mg of bovine serum albumin was dissolved in 0.667 ml PBS. 20 microliter of PEGNHS as a neat liquid and 20 microliter of albumin solution were mixed on a glass plate to form a uniform solution. Addition of 20 microliter 3M sodium hydroxide to PEGNHS-albumin mixture transformed the solution into soft hydrogel in 60 seconds. The resultant hydrogel was insoluble in water indicating formation of crosslinked network.

Example 13

Crosslinking of Proteins Solution Using Mixtures of Crosslinker

Crosslinking of Albumin Using PVPPANHS and BTANHS Mixture 333 mg of bovine serum albumin was dissolved in 0.667 ml PBS. 100 mg PEGNHS and 100 mg BTANHS were dissolved in 0.800 ml PBS. 20 microliter albumin solution and 20 microliter crosslinkers solution were mixed on a glass plate to form a uniform solution. Addition of 20 microliter 3M sodium hydroxide to crosslinker-albumin mixture transformed the solution into soft hydrogel in 60 seconds.

Example 14

Priming of Tissues Using Tissue Crosslinkers

Priming of Tissue Using PEGNHS Liquid Crosslinker

In this example that demonstrates how this method could be performed, 0.5 ml of PEGNHS crosslinker solution is applied to 2 cm2 bovine pericardium tissue (PEGNHS is used as a primer). A freshly prepared 1:1 mixture 30% albumin solution in PBS (pH 7) and 10% PVPPANHS solution in PBS is then applied over the primed area. The pH of the mixture is then raised by applying triethanol amine over the albumin solution. In a similar experiment, albumin solution is crosslinked on the tissue without the primer. The crosslinked albumin exhibits improved bonding to the tissue when used with the primer.

Example 15

Synthesis of Low Molecular Weight Degradable Crosslinker

Succinated Polyhydroxy Compounds Activated with N-hydroxysulfosuccinimide

In this example that demonstrates how this method could be performed, 10 g of erythritol is dissolved in 200 ml dry toluene. About 50 ml of toluene is distilled to remove traces of water from the erythritol. The solution is cooled to 50-60° C. and 20 ml pyridine and 8.58 g of succinic anhydride are added to the solution. The reaction mixture is then refluxed for 3 h and unreacted pyridine and toluene are evaporated to dryness under reduced pressure. The residue is used in activation reaction.

Part 2: Activation of ES with SNHS:

Erythritol-succinate (ES, 2.0 g) is dissolved in 10 ml of anhydrous dimethyl formamide ("DMF"), cooled to 0 C. 3.30 N,N-dicyclohexylcarbodiimide was added to the mixture followed by 3.47 g of N-hydroxysulfosuccinimide are added dropwise. After stirring the mixture overnight, the precipitated dicyclohexylurea is removed by filtration and the solution is concentrated by removing solvent. It is further purified by column chromatography.

Example 16

Synthesis of Water Soluble, Amine Reactive Polymerizable Monomer

Synthesis of N-sulfosuccinimidyl Methacrylate

In this example that demonstrates how this method could be performed, 3 g methacrylic acid, 14.4 g of N,N-dicyclohexylcarbodiimide (DCC), sodium salt and 50 ml dimethylformamide (DMF) are transferred to a 250 ml round bottom flask. The solution is cooled to 0° C. using ice bath. 15.2 g N-hydroxysulfosuccinimide dissolved in 50 ml dry DMF is added to the reaction mixture. The reaction mixture is kept at room temperature for 12 to 24 h. The reaction mixture is protected from moisture during the entire work up. At the end of the reaction, the precipitated dicyclohexylurea is removed by filtration. DMF from the reaction is removed by vacuum distillation. The crude product is further purified by column chromatography. The product is stored with 0.010 mg of hydroquinone as inhibitor. The product is soluble in water.

Example 17

Polymers and Copolymers of Water Soluble, Amine Reactive Monomer

Polymerization N-sulfosuccinimidyl Methacrylate

In this example that demonstrates how this method could be performed, 10 mg benzoyl peroxide, 1 gram n-sulfosuccinimidyl methacrylate and 3 ml DMF are transferred to a 20 ml polymerization tube. The tube is then heated at 70° C. for 5 h to 24 h in oil bath under nitrogen atmosphere. The polymerized product is recovered by adding the DMF solution to the large excess diethyl ether. In a similar manner, n-sulfosuccinimidyl methacrylate (0.2 gram) can be copolymerized with methyl methacrylate (0.8 gram, hydrophobic monomer) or n-vinyl pyrrolidinone (0.8 gram, hydrophilic monomer) using 10 mg benzoyl peroxide as initiator.

Example 18

Synthesis of Liquid Crosslinker (Biostable)

5 g Polyethylene glycol 600 diacid was dissolved in 50 ml dichloromethane and 50 ml tetrahydrofuran. The solution was cooled to 4° C. 4.9 g 1,3-dicyclohexyl carbodiimide (DCC) and 4.0 g n-hydroxysuccinimide were added to the reaction mixture. The mixture was stirred at 4° C. for 6 h and overnight at room temperature under nitrogen atmosphere. Dicyclohexylurea was removed by filtration and the PEG ester was by isolated by removing the solvents. It was further purified by column chromatography using alumina as a substrate and toluene as a mobile phase. The product was stored under nitrogen atmosphere at −20° C. The NHS ester product was a liquid at 25° C.

Example 19

Synthesis of Branched Liquid Crosslinker (Branched Polymer with 3 Reactive Groups) (Biodegradable)

Part 1: Conversion of PEG Hydroxy Groups into Carboxylic Groups.

1 In this example that demonstrates how this method could be performed, 5 g Polyethylene glycol triol, molecular weight 1000 (PEG-1000T) or trimethylolpropane ethoxylate (Sigma-Aldrich Product Number: 41,617-7) is dried at 60° C. overnight under vacuum prior to use. 10 g PEG-1000T copolymer is dissolved in 70 ml dry pyridine. 3.8 g of glutaric anhydride is added to it and the solution is refluxed for 2 h under nitrogen atmosphere. Most of the pyridine is distilled out and the polymer is isolated by pouring the cold pyridine solution to 4000 ml hexane and dried under vacuum at 60° C. and used immediately in subsequent carboxyl group activation reaction.

Part 2: Activation of Acid Group Using N-Hydroxysuccinimide.

To a solution of 10 g of PEG-1000T glutarate in 100 ml dry methylene chloride are added 2.8 g n-hydroxysuccinimide and 6.6 g DCC. The reaction mixture is cooled to 0° C. using ice bath and stirred overnight under nitrogen atmosphere. Dicyclohexylurea is removed by filtration. The filtrate is evaporated and the residue obtained is redissolved in 10 ml toluene. The toluene solution is precipitated in 2000 ml cold hexane.

Example 20

Liquid Crosslinkers—Mixture of Two Crosslinkers

In this example that demonstrates how this method could be performed, 1 g PEG 600 liquid crosslinker (Example 11) is mixed with 100 mg 4 arm-n-hydroxysuccinimide ester of polyethylene glycol carboxymethylene-butyric acid, average molecular weight 10000 Daltons (Shearwater 4 arm CM-HBA-NS-10K). The liquid mixture is used in crosslinking reaction with multifunctional amines and proteins

Example 21

Non-Aqueous Crosslinkable Composition—Polyethylene Glycol Based

In this example that demonstrates how this method could be performed, 5 g Polyethylene glycol dimethyl ether, molecular weight 400 (Sigma/Aldrich Product Number: 81311) is dried at 120 under vacuum for 24 h. 100 mg 4 arm-n-hydroxysuccinimide ester of polyethylene glycol carboxymethylene-butyric acid, average molecular weight 10000 Daltons (Shearwater 4 arm CM-HBA-NS-10K) is dissolved in dry 900 mg polyethylene glycol dimethyl ether, molecular weight 400. The solution is filter sterilized and is used in crosslinking reactions with polyfunctional amines such as amine terminated polyethylene glycol or trilysine or biological fluids such as blood, blood plasma or serum. The reaction can be carried out in situ. Polyethylene glycol dimethyl ether serves as a polymeric non-reactive, non-toxic, water soluble solvent for NHS ester.

Example 22

Non-Aqueous Liquid Crosslinkable Composition, Organic Solvent Based (N-Methyl Pyrrolidinone Based)

In this example that demonstrates how this method could be performed, 100 mg 4 arm-n-hydroxysuccinimide ester of polyethylene glycol carboxymethylene-butyric acid, average molecular weight 10000 Daltons (Shearwater 4 arm CM-HBA-NS-10K) is dissolved in dry 900 mg n-methyl pyrrolidinone. The solution is filter sterilized using 0.2 micron Teflon filter and is used in crosslinking reactions with polyfunctional amines such as amine terminated polyethylene glycol or trilysine or with biological fluids such as blood or blood serum. The amine and NHS ester should have same molar equivalent concentrations for efficient polymerization and crosslinking. The reaction can be carried out "in situ" using a minimally invasive surgical technique. N-methyl pyrrolidinone serves as a non reactive, non-toxic solvent for NHS ester.

Example 23

Gelation of Blood or Serum or Other Protein Containing Fluids Using Liquid Crosslinkers In this example that demonstrates how this method could be performed, 0.1 g of 4 arm NHS activated polyethylene glycol (4 arm-n-hydroxysuccinimide ester of polyethylene glycol carboxymethylene-butyric acid, average molecular weight 10000 Daltons (Shearwater 4 arm CM-HBA-NS-10K)) is dissolved 2 g PEG 600 NHS activated crosslinker (synthesized per Example 11). 100 mg of this solution is reacted with 200 microliter of ml fresh human blood. The proteins in the blood react with NHS ester and form a crosslinked hydrogel. The gel formation occurs in less than 2 minutes. The same crosslinking reaction can be carried out "in situ" during a MIS surgical or open surgical procedure. This gel formation or clotting represents an alternative path to natural blood clotting process.

Example 24

Synthetic Crosslinked Gels Made Using Liquid Crosslinkers

In this example that demonstrates how this method could be performed, 2.0 g (0.8 mM) of 8 arm branched-polyethylene glycol)-amine, average molecular weight 20000 Daltons (Shearwater 8ARM-NH2-20K) is dissolved in 10 ml 0.1 M sodium borate buffered pH 9.5. 0.318 g of PEG 600 NHS liquid ester (Example 11) is mixed with amine solution to produce a crosslinked gel. Gelation is seen to occur within 2 minutes after mixing the two solutions.

Example 25

Gelation of Blood or Blood Serum or Other Protein Containing Human Body Fluids Using a Non-Aqueous Crosslinker Solution In this example that demonstrates how this method could be performed, polyethylene glycol dimethyl ether, molecular weight 400 is dried under vacuum at 120° C. for 16 h to remove traces of moisture from the ether. The dry liquid polymeric ether is used as a solvent for PGG based 4 arm crosslinker. Briefly, 2 g PEG 10000 4 arm NHS ester (4 arm-n-hydroxysuccinimide ester of polyethylene glycol carboxymethylene-butyric acid, average molecular weight 10000 Daltons (Shearwater 4 arm CM-HBA-NS-10K)) is dissolved in ml 8 ml dry polyethylene glycol dimethyl ether 400. The solution is filter sterilized by 0.2 micron filter. 100 microliter of this solution is reacted with 200 microliter of ml fresh non citrated human blood. The proteins in the blood react with NHS ester and form a crosslinked hydrogel. The gel formation occurs in less than 2 minutes. The same crosslinking reaction can be carried out "in situ" during a MIS surgical or open surgical procedure. This gel formation or clotting represents an alternative path to natural thrombin based blood clotting process. The non-aqueous solution has good storage stability and does not require solution preparation in the operating room.

Example 26

Synthesis of Lysine Based Protein Crosslinker

Part 1: Synthesis of Lysine Succinimide
In this example that demonstrates how this method could be performed, 2 g of L-lysine is dissolved in 200 ml dry N,N-dimethyl formamide (DMF) in a 500 ml round bottom flask. 10.7 g succinic anhydride and 20 ml triethyl amine are added under nitrogen atmosphere. The mixture is heated to 60° C. for 6 h. At the end of 6 h period, the solution is cooled and solvent is removed by vacuum distillation. The crude product is purified by flash chromatography. It is then immediately used in next reaction.

Part 2: Activation of Carboxyl Groups with N-Hydroxysuccinimide Group
A 3 necked flask equipped with magnetic stirrer and nitrogen inlet is charged with 5 g Lysine Succinimide, 5.5 g of N-hydroxysuccinimide and 70 ml DMF. The solution is cooled 4° C. and 12.7 of 1,3-dicyclohexyl carbodiimide dissolved in 30 ml DMF are added under nitrogen atmosphere. The mixture is stirred at 4° C. for 6 h and overnight at room temperature under nitrogen atmosphere. Dicyclohexylurea is removed by filtration and NHS derivative is by isolated by removing the DMF under vacuum. The NHS ester is purified by column chromatography.

Example 27

Synthesis of Lysine Glutaramide NHS Ester

Part 1: Synthesis of Lysine Glutaramide
In this example that demonstrates how this method could be performed, 5 g Lysine, 8.7 g glutaric anhydride and 2.0 g 4-Dimethylaminopyridine (DMAP) are weighed into a 100 ml flask fitted with a condenser and nitrogen inlet. 100 ml DMF is added and the mixture stirred under nitrogen atmosphere for 5 min and immersed into an oil bath preheated to 90° C. for 1.5 h until HPLC assay indicated completion of reaction. DMF is evaporated under vacuum (distilled below 40° C. and the residue is used directly for the subsequent reaction. The residue can be purified by chromatography on silica gel.

Part 2: Activation of Lysine Glutaramide Acid Groups Using NHS Ester
5 g lysine glutaramide and 5.1 g n-hydroxysuccinimide are dissolved in 100 ml methylene chloride. The mixture is stirred for 5 min under nitrogen atmosphere, and then 11.7 g DCC is added in one portion. Stirring under nitrogen is continued for 16 hr until HPLC analysis indicated completion of the reaction. The reaction mixture is filtered to remove Dicyclohexylurea. The insoluble dicyclohexylurea is ished with 35 ml dichloromethane. The combined filtrate is collected in a reaction vessel. The reaction mixture is evaporated in vacuo. The product is purified by column chromatography on silica.

Example 28

Synthesis of Ethylene Diamine Succinimide NHS Ester

Synthesis of Ethylene Diamine Succinimide
This example that demonstrates how this method could be performed. Part 1: In a 250 ml round bottom flask, 2 g of ethylene diamine is dissolved in 50 ml dry pyridine and 50 ml benzene. 7.3 g succinic anhydride is added under nitrogen atmosphere. The mixture is refluxed under nitrogen atmosphere for 6 h and solvent is removed by vacuum distillation. The crude product is purified by flash chromatography or recrystallization. It is then immediately used in next reaction.

Part 2: Activation of Carboxyl Groups with N-Hydroxysuccinimide Group
A 3 necked flask equipped with magnetic stirrer and nitrogen inlet is charged with 5 g ethylene diamine succinimide and 100 ml dichloromethane (DCM). The solution is cooled 4° C. and 4.9 of N-hydroxysuccinimide and 11.2 g of 1,3-dicyclohexyl carbodiimide (DCC) are added under nitrogen atmosphere. The mixture is stirred at 4° C. for 6 h and overnight at room temperature under nitrogen atmosphere. Dicyclohexylurea is removed by filtration and the NHS ester is by isolated by removing the DCM under vacuum. The NHS ester is purified by column chromatography or recrystallization.

Example 29

Hydroxylamine Succinate NHS Ester

Hydroxylamine Succinate
This example that demonstrates how this method could be performed. Part 1: To a solution of 2 g hydroxy amine in 100 ml dry benzene and 100 ml pyridine, 9.4 g succinic anhydride is added and the reaction mixture stirred at room temperature for 2 h and refluxed for 2 h. The solvent is evaporated under vacuum and the residue is purified by flash chromatography using silica gel.

Part 2: Hydroxylamine Succinate NHS Ester
Part 2: To a cold (4° C.) solution of 5 g Hydroxylamine Succinate and 5. 1 g n-hydroxysuccinimide in 120 DMF, 11.8 g 1,3-dicyclohexyl carbodiimide in 30 ml of DMF and is added under nitrogen atmosphere. The reaction is continued at room temperature for 8 h and urea precipitate is filtered. The filtrate is evaporated the crude compound is recovered. The compound is further purified by flash chromatography.

Example 30

Synthesis of Aspartic Acid Succinimide NHS Ester

Part 1: Synthesis of Aspartic Acid Succinimide
This example that demonstrates how this method could be performed. 9.4 g aspartic acid, 10 ml triethyl amine and 100 ml tetrahydrofuran are transferred into a 100 ml flask fitted with a condenser and nitrogen inlet. The mixture is cooled to 0° C. and 5 g succinyl chloride is added and the mixture stirred under nitrogen atmosphere for 5 min and refluxed for 6 hours. The triethyl amine hydrochloride is filtered and the filtrate is concentrated by removing the solvent under vacuum. The residue is used directly for the subsequent reaction. The residue can be purified by chromatography on silica gel.

Part 2: Activation of Aspartic Acid Succinimide Acid Groups Using NHS Ester
2 g aspartic acid succinimide and 2.9 g n-hydroxysuccinimide are dissolved in 100 ml methylene chloride. The mixture is stirred for 5 min under nitrogen atmosphere, and then 6.7 g 1,3-dicyclohexyl carbodiimide is added in one portion. Stirring under nitrogen is continued for 16 hr until HPLC analysis indicated completion of the reaction. The reaction mixture is filtered to remove dicyclohexylurea. The insoluble dicyclohexylurea is washed with 35 ml dichloromethane. The combined filtrate is collected in a reaction vessel. The reaction mixture is evaporated in vacuo. The product is purified by column chromatography on silica.
15 mg of Crosslinker Dissolved Completely 1 ml Water or PBS Solution.

Example 31

Synthesis of Aspartic Acid Based Protein Crosslinker

Part 1: Synthesis of Aspartic Acid Sebaciamide
This example that demonstrates how this method could be performed. In a 500 ml round bottom flask, 5 g aspartic acid and 10 ml triethyl amine are dissolved in 100 ml dry tetrahydrofuran. The solution is cooled to 0° C. using ice bath and 10.7 g succinyl chloride is added dropwise under nitrogen atmosphere. The mixture is heated to 60° C. under nitrogen atmosphere for 6 h. At the end of 6 h period, the solution is cooled and solvent is removed by vacuum distillation. The crude product is purified by flash chromatography. It is then immediately used in next reaction.

Part 2: Activation of Carboxyl Groups with N-Hydroxysuccinimide
A 3 necked flask equipped with magnetic stirrer and nitrogen inlet is charged with 5 g aspartic acid sebaciamide, 5.5 g of N-hydroxysuccinimide and 70 ml dichloromethane. The solution is cooled 4° C. and 12.7 of 1,3-dicyclohexyl carbodiimide dissolved in 30 ml dichloromethane is added under nitrogen atmosphere. The mixture is stirred at 4° C. for 6 h and overnight at room temperature under nitrogen atmosphere. Dicyclohexylurea is removed by filtration and NHS derivative is by isolated by removing the dichloromethane. The NHS ester is purified by column chromatography.

Example 32

Hydroxylamine Glutarate NHS Ester

Hydroxylamine Glutarate
This example that demonstrates how this method could be performed. Part 1: To a solution of 2 g hydroxy amine in 100 ml dry benzene and 20 ml triethyl amine, 9.4 g glutaric anhydride is added and the reaction mixture stirred at room temperature for 2 h and refluxed for 2 h. The solvent is evaporated under vacuum and the residue is purified by flash chromatography using silica gel.

Part 2: Hydroxylamine Glutarate NHS Ester
Part 2: To a cold (4° C.) solution of 5 g Hydroxylamine Succinate and 5.1 g n-hydroxysuccinimide in 120 ml dichloromethane, 11.8 g 1,3-dicyclohexyl carbodiimide in 30 ml of dichloromethane is added under nitrogen atmosphere. The reaction is continued at room temperature for 8 h and urea precipitate is filtered. The filtrate is evaporated the crude compound is recovered. The compound is further purified by flash chromatography.

Example 33

Crosslinking of Protein Using Crosslinkers

Method 1: Crosslinking Protein at Physiological Conditions (20 mM Phosphate Buffer Solution, pH 7.2)
This example that demonstrates how this method could be performed. 1 g of bovine albumin is dissolved in 1 ml phosphate buffer solution (20 mM PBS, pH 7.4). 100 mg aspartic acid succinimide NHS ester (Example 30) is dissolved in 1 ml PBS solution (20 mM PBS, pH 7.4). Both the solutions are mixed in 50 ml polypropylene tube. The crosslinked gel formation is noticed in less than 30 minutes.

Method 2: Crosslinking of Protein at Non-Physiological pH
This example that demonstrates how this method could be performed. 1 g of bovine albumin is dissolved in 2 ml borate buffer (10 mM, pH 9.5). 100 mg Lysine Succinimide NHS ester (Example 1) is dissolved in 1 ml 10 mM phosphate buffer, pH 4.0. 1 ml of each solution are mixed in a 50 ml polypropylene centrifuge tube. The gel formation is noticed in less than 30 minutes.

Albumin and Other Protein Crosslinking can be Done "In Situ" Inside a Body Cavity or on Tissue Surface.

Method 34

Crosslinking of Collagen (Bovine Pericardium Tissue)

This example that demonstrates how this method could be performed. Bovine pericardial sack is obtained from a local abbotair and is cleaned to remove blood and fatty tissue from the surface. Ten 1 cm by 1 cm pieces are cut from a bovine pericardial sack and transferred to 10 ml 20 mM phosphate buffer solution (PBS, pH 7.2).

100 mg aspartic acid succinimide NHS ester (example 5) is added to the tissue/PBS mixture. The solution is vortexed for 5 minutes and tissue is incubated at room temperature for 12 hours. The tissue is separated from the crosslinker mixture and washed with 20 ml PBS solution 3 times to remove unreacted crosslinker. The crosslinked collagen or tissue shows high shrink temperature indicating crosslinking of the tissue.

Example 35

Crosslinking of Synthetic Polymer

Formation of Crosslinked Biostable Gels

This example that demonstrates how this method could be performed. 1.3 g of 8 arm branched-polyethylene glycol-amine, average molecular weight 20000 Daltons (Shearwater 8ARM-NH2-20K) is dissolved in 5 ml 0.1 M sodium borate buffered pH 9.5. 0.09 g aspartic acid succinimide NHS ester (Example 5) is dissolved in 5 ml phosphate buffered saline. 1 ml of each of these two solutions are mixed to produce a crosslinked gel. In another variation of this method, 0.09 g aspartic acid succinimide NHS ester (Example 5) is directly added to the amine terminated polymer solution to produce a crosslinked polymer.

Example 36

Crosslinking of Synthetic Polymer (Formation of Crosslinked Biodegradable Gel)

Gel Based on Succinate Ester Link

This example that demonstrates how this method could be performed. 1.3 g of 8 arm branched-polyethylene glycol-amine, average molecular weight 20000 Daltons (Shearwater 8ARM-NH2-20K) is dissolved in 5 ml 0.1 M sodium borate buffered pH 9.5. 0.12 g Hydroxylamine Succinate NHS ester (Example 4) is dissolved in 5 ml phosphate buffered saline. 1 ml of each of these two solutions are mixed to produce a crosslinked gel. The crosslinked gel degrades due to hydrolysis of succinate ester bond in Hydroxylamine Succinate NHS ester.

Gel Based on Glutarate Based Link 1.3 g of 8 arm branched-polyethylene glycol-amine, average molecular weight 20000 Daltons (Shearwater 8ARM-NH2-20K) is dissolved in 5 ml 0.1 M sodium borate buffered pH 9.5. 0.12 g Hydroxylamine Glutarate NHS ester (Example 7) is dissolved in 5 ml phosphate buffered saline. 1 ml of each of two solutions are mixed to produce a crosslinked gel. The crosslinked gel degrades due to hydrolysis of glutarate ester bond in Hydroxylamine Glutarate NHS ester.

Example 37

Controlled Release of Drug from Crosslinked Gels

Controlled Release of Heparin from Crosslinked Gel

This example that demonstrates how this method could be performed. 1.3 g (0.7 mM) of 8 arm branched-polyethylene glycol-amine, average molecular weight 20000 Daltons (Shearwater 8ARM-NH2-20K) and 0.3 g heparin are dissolved in 5 ml 0.1 M sodium borate buffered pH 9.5. 0.12 g Hydroxylamine Succinate NHS ester (Example 4) is dissolved in 5 ml phosphate buffered saline. 1 ml of each of these two solutions are mixed to produce a crosslinked gel. The release of heparin from the crosslinked gel is monitored at 37° C. in PBS.

The invention has been described herein with respect to particular embodiments having various features. The features of these embodiments may be mixed-and-matched to form other combinations as guided by the need to make an operable device.

What is claimed is:

1. A low molecular weight precursor comprising: a biocompatible liquid crosslinker with a molecular weight of no more than about 2000 Daltons that comprises at least three activated acid functional groups that are strong electrophiles selected from the group consisting of succinimide, succinimide ester, N-hydroxysuccinimide ester and maleimide, wherein the crosslinker forms a melt at less than about 50° C., wherein the strong electrophiles are not reactable by a Michaels-type reaction.

2. The precursor of claim 1, wherein the crosslinker is a polyethylene glycol derivative.

3. The precursor of claim 1 further comprising a hydrolytically degradable group.

4. The precursor of claim 1, wherein the functional groups are N-hydroxysuccinimide or N-hydroxysulfosuccinimide.

5. The precursor of claim 1, wherein the molecular weight is between about 300 and about 1000 Daltons.

6. The precursor of claim 1, wherein the crosslinker is a melt at about 10° C. to about 50° C.

7. The precursor of claim 1, wherein the crosslinker comprises polyethylene glycol.

8. The precursor of claim 1, wherein the crosslinker consists essentially of a polyethylene glycol in which each of at least three end groups has been replaced with one of the functional groups.

9. The precursor of claim 8 wherein the crosslinker further comprises a hydrolytically degradable group.

10. The precursor of claim 9 wherein the functional groups are succinimides.

11. The precursor of claim 10 wherein the crosslinker is a melt at about 10° C. to about 50° C.

12. The precursor of claim 11, wherein the molecular weight is between about 300 and about 1000 Daltons.

* * * * *